United States Patent
Rush et al.

(10) Patent No.: US 10,496,886 B1
(45) Date of Patent: *Dec. 3, 2019

(54) MEDICAL ENVIRONMENT MONITORING SYSTEM

(71) Applicant: OCUVERA LLC, Lincoln, NE (US)

(72) Inventors: Benjamin D. Rush, Lincoln, NE (US); Joshua M. Brown-Kramer, Lincoln, NE (US); Lucas A. Sabalka, Lincoln, NE (US); Brian S. Gansemer, Lincoln, NE (US); Clay T. Upton, Lincoln, NE (US); Paul B. Bauer, Lincoln, NE (US); Andrew R. Unterseher, Lincoln, NE (US); Benjamin J. Origas, Lincoln, NE (US); Douglas W. Durham, Lincoln, NE (US)

(73) Assignee: Ocuvera LLC, Lincoln, NE (US)

( * ) Notice: Subject to any disclaimer, the term of this patent is extended or adjusted under 35 U.S.C. 154(b) by 276 days.

This patent is subject to a terminal disclaimer.

(21) Appl. No.: 15/392,222

(22) Filed: Dec. 28, 2016

Related U.S. Application Data

(63) Continuation of application No. 14/055,139, filed on Oct. 16, 2013, now Pat. No. 9,538,158.

(60) Provisional application No. 61/714,252, filed on Oct. 16, 2012, provisional application No. 61/826,669, filed on May 23, 2013, provisional application No. 61/880,273, filed on Sep. 20, 2013.

(51) Int. Cl.
*G06K 9/00* (2006.01)
*G06T 7/73* (2017.01)
*G08B 21/04* (2006.01)

(52) U.S. Cl.
CPC ..... *G06K 9/00771* (2013.01); *G06K 9/00335* (2013.01); *G06K 9/00369* (2013.01); *G06T 7/73* (2017.01); *G08B 21/0476* (2013.01); *G06T 2207/20076* (2013.01); *G06T 2207/30196* (2013.01)

(58) Field of Classification Search
CPC .............. A61B 5/1115; G06K 9/00771; G06K 9/00335; G08B 21/043; G08B 21/0476; G06T 7/73
See application file for complete search history.

(56) References Cited

U.S. PATENT DOCUMENTS

| | | | |
|---|---|---|---|
| 7,110,569 B2 | 9/2006 | Brodsky et al. | |
| 7,541,934 B2 | 6/2009 | Fredriksson et al. | |
| 7,612,666 B2 | 11/2009 | Badawy | |
| 8,675,920 B2 | 3/2014 | Hanson et al. | |
| 9,041,810 B2 | 5/2015 | Ecker et al. | |

(Continued)

OTHER PUBLICATIONS

Girshick, Ross et al., "Efficient Regression of General-Activity Human Poses from Depth Images", Publication, Oct. 2011, 8 pages.

(Continued)

*Primary Examiner* — Patrick Fernandes
(74) *Attorney, Agent, or Firm* — Bejin Bieneman PLC

(57) ABSTRACT

A system and a method are described for monitoring a medical care environment. In one or more implementations, a method includes identifying a first subset of pixels within a field of view of a camera as representing a bed. The method also includes identifying a second subset of pixels within the field of view of the camera as representing an object (e.g., a subject, such as a patient, medical personnel; bed; chair; patient tray; medical equipment; etc.) proximal to the bed. The method also includes determining an orientation of the object within the bed.

18 Claims, 21 Drawing Sheets

(56) References Cited

U.S. PATENT DOCUMENTS

| | | |
|---|---|---|
| 9,129,506 B1 | 9/2015 | Kusens |
| 9,159,215 B1 | 10/2015 | Kusens |
| 9,165,449 B2 | 10/2015 | Ribble et al. |
| 9,204,823 B2 | 12/2015 | Derenne et al. |
| 9,277,878 B2 | 3/2016 | McClure et al. |
| 9,311,540 B2 | 4/2016 | Ecker et al. |
| 9,538,158 B1 | 1/2017 | Rush et al. |
| 2014/0022081 A1 | 1/2014 | Ribble et al. |
| 2014/0313340 A1 | 10/2014 | Ecket et al. |

OTHER PUBLICATIONS

Johnson, Rose et al., "Exploring the Potential for Touchless Interaction in Image Guided Interventional Radiology", Publication, May 2011, 10 pages.

Ni, Bingbing et al., "RGBD-Camera Based Get-Up Event Detection for Hospital Fall Prevention", Acoustics, Speech and Signal Processing (ICASSP), 2012 IEEE International Conf. Mar. 2012, pp. 1405-1408.

Sharp, Toby, "Implementing Decision Trees and Forests on a GPU", Publication, 2008, 14 pages.

Shotton, Jamie et al., "Real-Time Human Pose Recognition in Parts from a Single Depth Image", Publication, Jun. 2011, 8 pages.

Shotton, Jamie et al., "TextonBoost for Image Understanding: Multi-Class Object Recognition and Segmentation by Jointly Modeling Texture, Layout and Context", Publication, Jan. 2009.

Shotton, Jamie et al., "Semantic Texton Forests for Image Categorization and Segmentation", Publication, 2008, 8 pages.

U.S. Appl. No. 15/061,323, Rush et al., filed Mar. 4, 2016.

U.S. Appl. No. 15/210,478, Rush et al., filed Jul. 14, 2016.

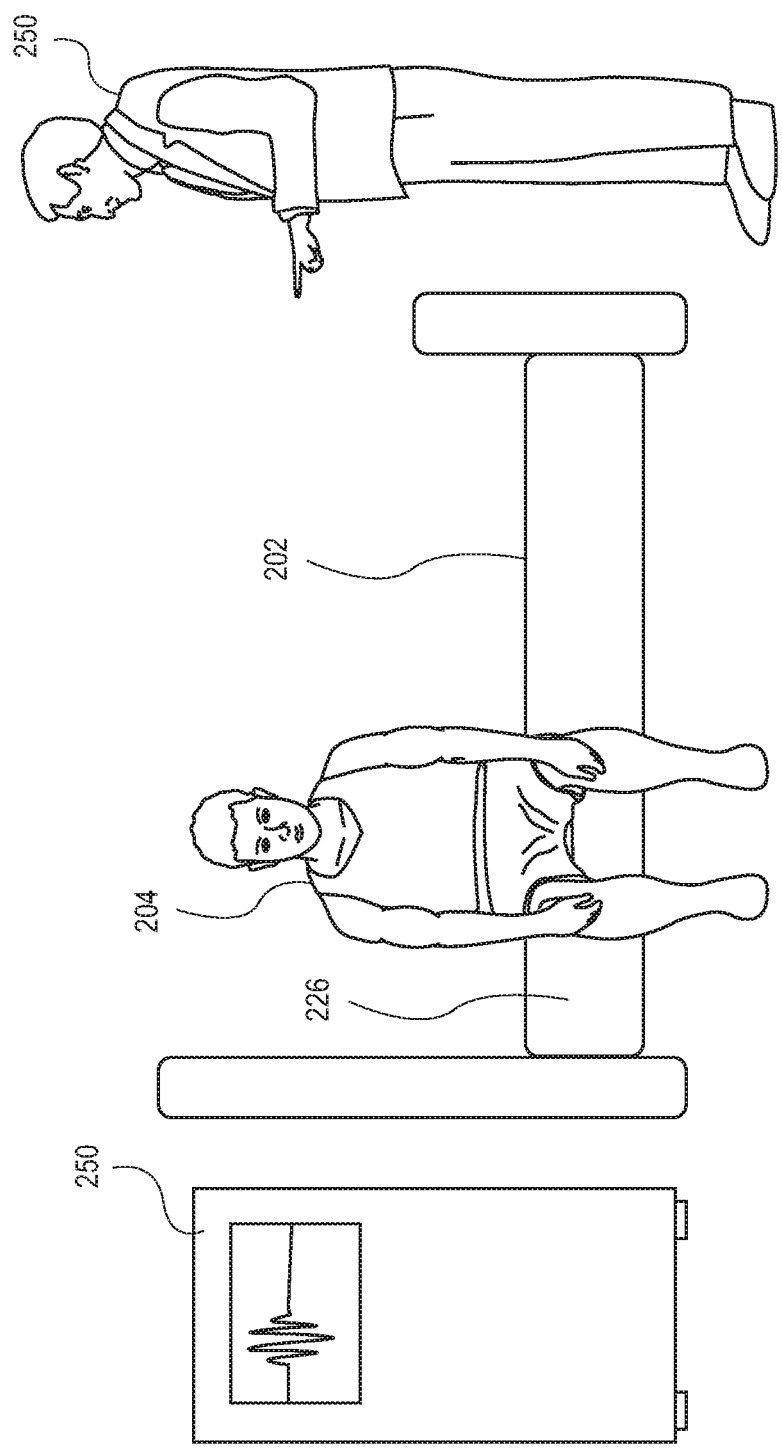

MEDICAL ENVIRONMENT MONITORING SYSTEM

CROSS-REFERENCE TO RELATED APPLICATIONS

The present application is a continuation under 35 U.S.C. § 120 of U.S. patent application Ser. No. 14/055,139, filed Oct. 16, 2013, entitled "MEDICAL ENVIRONMENT MONITORING SYSTEM," which is hereby incorporated by reference in its entirety.

BACKGROUND

Cameras are configured to capture images within the camera's field-of-view. Cameras may be configured to capture data representing color frame images, such as Red-Green-Blue cameras, and/or configured to capture data representing depth frame images. In some configurations, cameras configured to capture depth frame data transmit a near-infrared light over a portion of the camera's field-of-view and determine a time of flight associated with the transmitted light. In other implementations, the depth may be determined by projecting a structured pattern of infrared light and determining depth from an infrared camera utilizing suitable parallax techniques.

SUMMARY

A system and a method are described for monitoring a medical care environment. For example, a system and a method are described for monitoring a patient proximal to a bed or chair to detect the patient orientation and patient activity levels. In one or more implementations, the method includes identifying a first subset of pixels within a field of view of a camera as representing a bed. The system or method also includes identifying a second subset of pixels within the field of view of the camera as representing an object (e.g., a subject, such as a patient, medical personnel; bed; chair; patient tray; medical equipment; etc.) proximal to the bed. The method also includes determining an orientation of the object within the bed.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The detailed description is described with reference to the accompanying figures. The use of the same reference numbers in different instances in the description and the figures may indicate similar or identical items.

DETAILED DESCRIPTION

Example Monitoring Implementation

Figure 1:
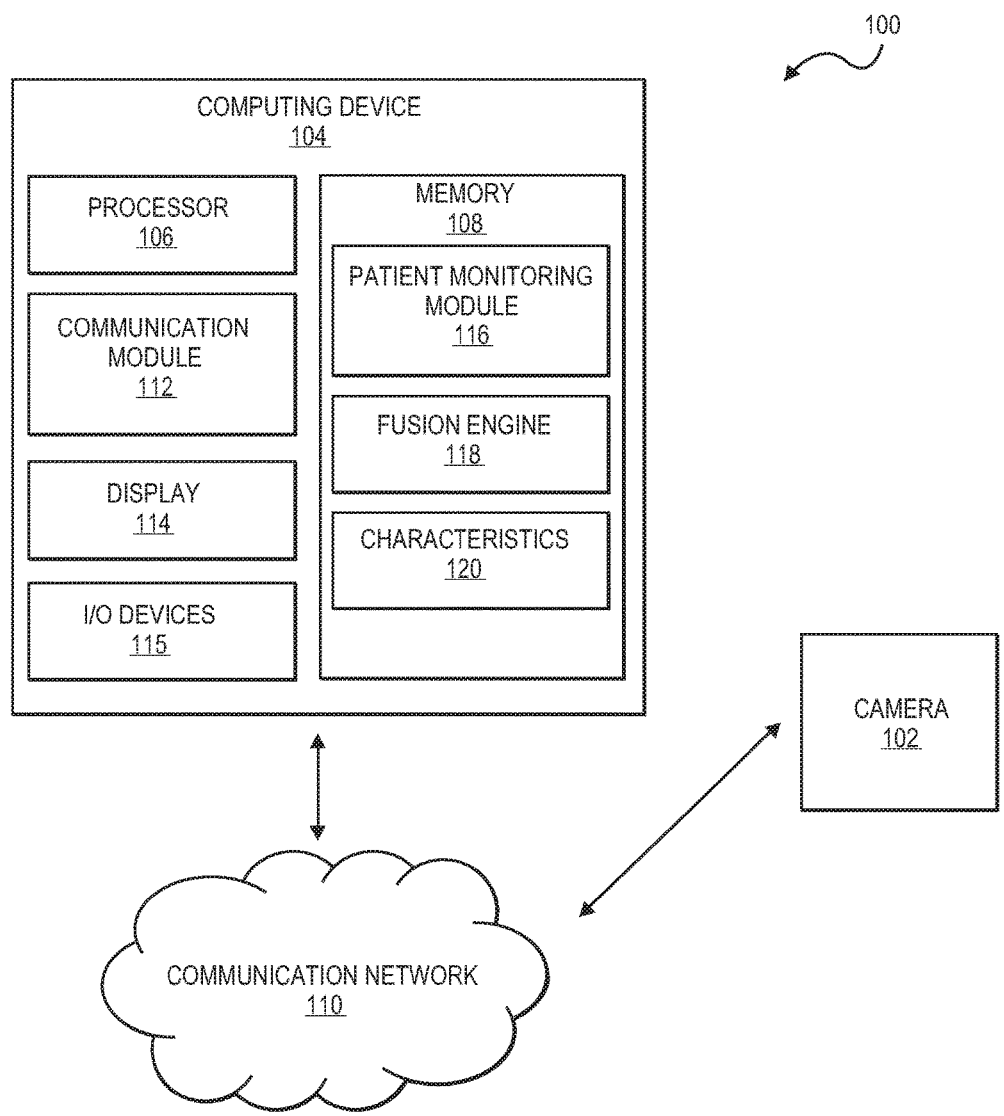
FIG. 1 is a block diagram of an image capture system in accordance with an example implementation of the present disclosure.

FIG. 1 illustrates an image capture system 100 in accordance with an example implementation of the present disclosure. As shown, the image capture system 100 includes one or more image capture devices (e.g., one or more cameras 102) and a computing device 104 communicatively coupled to the image capture devices. The cameras 102 are configured to capture images and per-pixel depth information in a field-of-view (FOV) of the cameras 102. As described below, the one or more cameras 102 may be integral with the computing device 104 in some implementations or the one or more cameras 102 may be external to the computing device 104 in other implementations. In an implementation, the cameras 102 may be depth cameras, such as Red-Green-Blue depth (RGB-D) cameras operable to capture depth frame image data representing one or more depth frame images and to capture color frame image data representing one or more color (RGB) frame images. In an embodiment, the cameras 102 may include, but are not limited to: a near infrared light configured to generate a near infrared light pattern onto the objects within the FOV, a depth frame image complementary-metal-oxide-semiconductor (CMOS) sensor device configured to measure the depth of each object within the FOV, and a color frame image CMOS camera device. For example, RGB-D cameras can identify various objects within the FOV of the cameras 102 and estimate the depth of the identified objects through various depth approximation techniques. For instance, the RGB-D cameras may transmit a structured light pattern in the near-infrared spectrum and utilize suitable parallax techniques to estimate the depth of the objects within the camera's 102 FOV in order to generate depth image data representing one or more depth frame images. Thus, a camera 102 captures data to allow for generation of a depth frame image representing at least partially objects within the camera's 102 FOV. The camera 102 may also be configured to capture color frame image data representing a color frame image at least partially representing objects within the camera's 102 FOV. For example, the depth image may include a two-dimensional (2-D) pixel area of the captured scene where each pixel in the 2-D pixel area may represent a depth value such as a length or distance (e.g., centimeters, millimeters, or the like of an object in the captured scene from the camera 102)

In an implementation, the camera 102 provides the ability to capture and map three-dimensional video imagery in addition to two-dimensional video imagery. For example, the camera 102 can capture two-dimensional data for a plurality of pixels that comprise the video image. These data values represent color values for the pixels (e.g., red, green, and blue [RGB] values for each pixel that represents the environment). Thus, objects captured by the cameras 102 can appear as two-dimensional objects via a monitor. As mentioned above, the cameras 102 can also capture depth data within the cameras' 102 FOV. Thus, the cameras 102 are configured to capture the x and y components (e.g., x and y values) of the environment within the FOV using RGB values (captured image data) for each pixel in the scene.

However, the cameras 102 are configured to also capture the z-components of the environment, which represent the depth values (e.g., depth estimate data corresponding to the z-axis) within the environment.

The camera 102 furnishes the image data (captured image data, depth estimate data, etc.) to the computing device 104. In a specific implementation, the camera 102 may be configured to capture images representing environmental views within the FOV of the camera 102. For example, the camera 102 may capture image data (e.g., three-dimensional data) representing a bed and one or more objects within the FOV of the camera 102 with respect to an image plane of the camera 102.

The computing device 104 may be configured in a variety of ways. For example, the computing device 104 may be a server computing device, a desktop computing device, a laptop computing device, an embedded computing device, or the like. In some implementations, the camera 102 is external to the computing device 104. In other implementations, the camera 102 is integral with the computing device 104. As shown in FIG. 1, the computing device 104 includes a processor 106 and a memory 108.

The processor 106 provides processing functionality for the computing device 104 and may include any number of processors, micro-controllers, or other processing systems and resident or external memory for storing data and other information accessed or generated by the computing device 104. The processor 106 may execute one or more software programs (e.g., modules) that implement techniques described herein. For example, the processor 106, in conjunction with one or more modules as described herein, is configured to generate a depth mask (image) of the environment based upon the depth estimate data (e.g., z-component data) captured by the cameras 102. For example, one or more modules are configured to cause the processor 106 to continually monitor the depth value of at least substantially all of the pixels that represent the captured environment and stores the greatest (deepest) depth value associated with each pixel. For instance, the modules cause the processor 106 to continually monitor for a pre-determined amount of time (e.g., a plurality of frames) the depth value of the pixels and stores the deepest depth value measured during the time interval. Thus, the depth mask comprises an accumulation of depth values and each value represents the deepest depth value of a pixel measured over the time interval. The processor 106 can then be instructed to generate a point cloud based upon the depth mask that includes a set of point values that represent the captured environment.

The memory 108 is an example of tangible computer-readable media that provides storage functionality to store various data associated with the operation of the computing device 104, such as the software program and code segments mentioned above, or other data to instruct the processor 106 and other elements of the computing device 104 to perform the steps described herein.

The computing device 104 is communicatively coupled to the cameras 102 over a communication network 110 through a communication module 112 included in the computing device 104. The communication module 112 may be representative of a variety of communication components and functionality, including, but not limited to: one or more antennas; a browser; a transmitter and/or receiver; a wireless radio; data ports; software interfaces and drivers; networking interfaces; data processing components; and so forth.

The communication network 110 may comprise a variety of different types of networks and connections that are contemplated, including, but not limited to: the Internet; an intranet; a satellite network; a cellular network; a mobile data network; wired and/or wireless connections; and so forth.

Examples of wireless networks include, but are not limited to: networks configured for communications according to: one or more standard of the Institute of Electrical and Electronics Engineers (IEEE), such as 802.11 or 802.16 (Wi-Max) standards; Wi-Fi standards promulgated by the Wi-Fi Alliance; Bluetooth standards promulgated by the Bluetooth Special Interest Group; and so on. Wired communications are also contemplated such as through universal serial bus (USB), Ethernet, serial connections, and so forth.

The system 100 may include a display 114 to display information to a user of the computing device 104. In embodiments, the display 114 may comprise an LCD (Liquid Crystal Diode) display, a TFT (Thin Film Transistor) LCD display, an LEP (Light Emitting Polymer) or PLED (Polymer Light Emitting Diode) display, and so forth, configured to display text and/or graphical information such as a graphical user interface. The processor 106 is configured to request depth image data and color frame image data from the camera 102 (e.g., image capture device) and create an association between the depth image data and the color frame image data. In an implementation, the processor 106 may be configured to provide the associated data to the display 114 for display purposes.

As shown in FIG. 1, the system 100 may include one or more input/output (I/O) devices 115 (e.g., a keypad, buttons, a wireless input device, a thumbwheel input device, a trackstick input device, a touchscreen, and so on). The I/O devices 115 may include one or more audio I/O devices, such as a microphone, speakers, and so on.

As shown in FIG. 1, the computing device includes a patient monitoring module 116 which is storable in the memory 108 and executable by the processor 106. The patient monitoring module 116 is representative of functionality to monitor a medical care environment. For example, the module 116 is representative of functionality to monitor one or more objects (e.g., subjects) within a medical environment. For instance, the objects may be patients, medical personnel, medical equipment, and so forth. In a specific implementation, the module 116 represents functionality to monitor a patient when the patient is positioned proximal or within a bed (or chair). While the present disclosure illustrates a patient in or proximal to a bed, it is understood that the system 100 may utilize the techniques disclosed within to monitor a patient in or proximal to a chair. The module 116 is configured to determine whether the patient is still in the bed (or the chair) and the approximate orientation (e.g., positioning) of the patient within the bed (or the chair). The system 100 may be utilized to monitor a patient within a medical care environment, such as a hospital environment, a home environment, or the like. The module 116 also represents functionality to monitor medical personnel within the medical environment (e.g., monitor how long the medical personnel is within the FOV). The module 116 may monitor the objects within the medical environment through a variety of techniques, which are described in greater detail below.

Figure 2A:
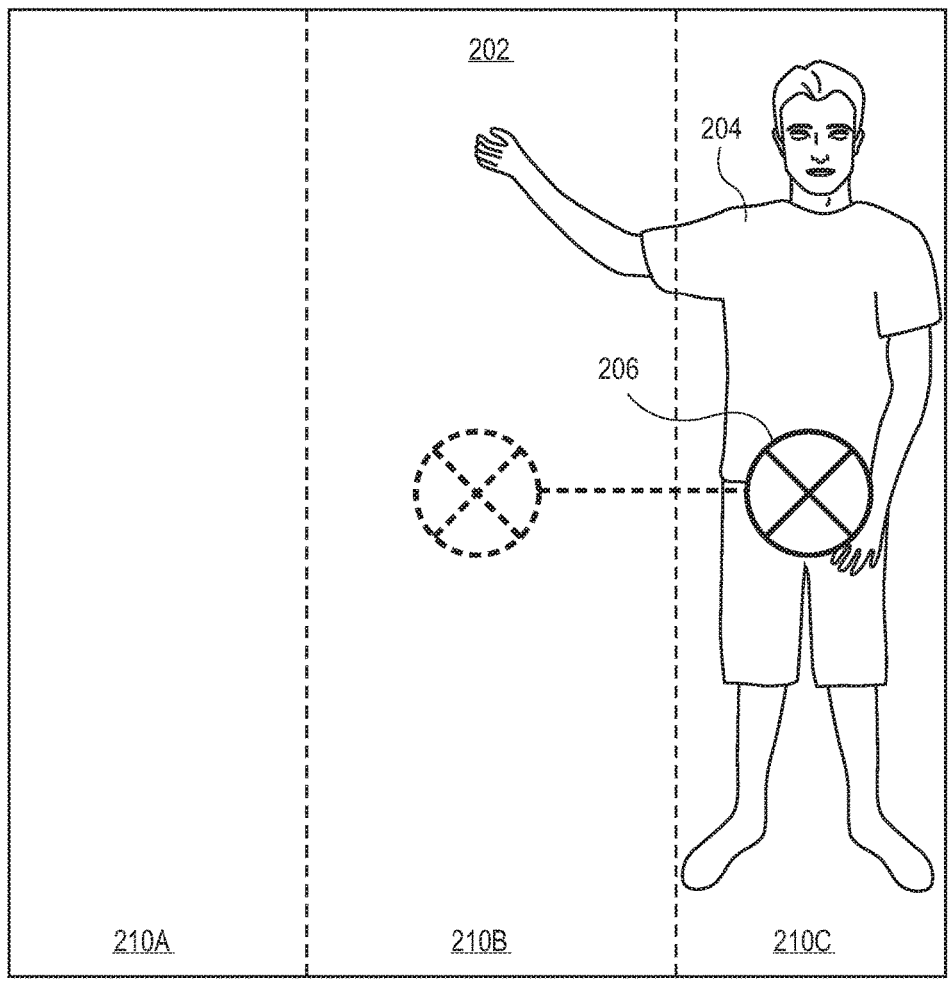
FIGS. 2A through 2Z are diagrammatic illustrations depicting various techniques for monitoring an object within a physical environment according to the image capture system shown in FIG. 1.

The module 116 is configured to cause the processor 106 to determine a depth value associated with each pixel (e.g., each pixel has a corresponding value that represents the approximate depth from the camera 102 to the detected object). In an implementation, the module 116 is configured to cause the processor 106 to determine a center of mass of a detected object positioned above the bed plane. For example, the module 116 may initially cause the processor 106 to determine a bed plane 202 representing a bed within the FOV of the camera 102 (e.g., determine the depth of the bed with no objects on or over the bed). Thus, the pixels associated with the bed are identified (i.e., define a bed plane) and an associated distance is determined for the identified bed. When an object is positioned within in the bed, the module 116 is configured to cause the processor 106 to continually monitor the depth values associated with at least substantially all of the pixels within the defined bed plane. Thus, the processor 106 is configured to process the depth image to determine one or more targets (e.g., users, patients, bed, etc.) are within the captured scene. For instance, the processor 106 may be instructed to group together the pixels of the depth image that share a similar distance As shown in FIG. 2A, at least a portion of the pixels proximal to the bed 202 may represent an object 204 (e.g., a patient) within the bed, and the module 116 causes the processor 106 to monitor the depth values of the pixels representing the object 204 as these pixels have a depth value that is less than the depth value of the pixels defining the bed plane 202 (e.g., the object is nearer to the camera 102 as compared to the top plane of the bed, the object is above the bed plane). The module 116 causes the processor 106 to identify a group of pixels having depth values (e.g., z-values) indicating a closer distance to the camera 102 as compared to the pixels defining the bed plane 202. For example, the processor 106 may incorporate a shortest-distance technique for identifying these pixels. The module 116 causes the processor 106 to determine a center of mass 206 based upon the identified pixels (pixels having z-value closer to the camera 102 as compared to the pixels representing the bed plane). The module 116 is configured to instruct the processor 106 to divide the bed into discrete portions. For example, the module 116 may be configured to divide the bed into three (3) discrete portions 210A, 210B, 210C (i.e., 2 side portions and 1 middle portion). The module 116 then instructs the processor 106 to determine whether more than half of the mass (approximated), or center of mass 206, of the object 204 is within one of the outer thirds of the bed. If at least approximately half of the mass is determined to be within a side portion of the bed, the processor 106 determines that the patient is at the edge of the bed. Based upon this determination, the module 116 causes the issuance of an alert (e.g., electronic communication such as a SMS message, an e-mail message, or the like) to detect, or to indicate, that the patient is near the edge of the bed.

Figure 2B:
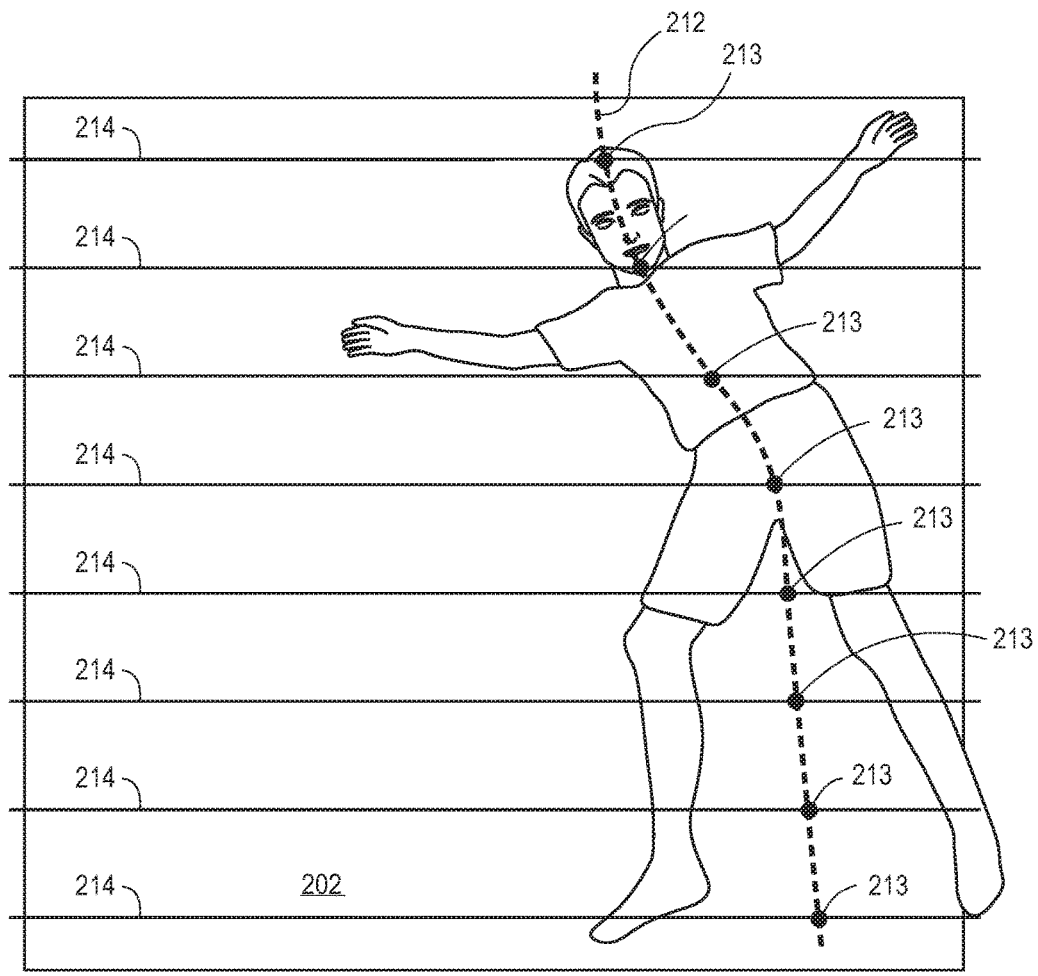

In another implementation, the module 116 may utilize center of mass scan-line techniques, or other suitable techniques, to determine how the patient is positioned within the bed (see FIG. 2B). In an implementation, the module 116 is configured to generate a curve 212 representing an orientation of the object 204 (e.g., patient's body) within the bed. If the bottom portion of the curve 212 moves to the right with respect to a defined center line and then moves back to the center line, the module 116 determines that the patient is positioned on the patient's left side with his or her knees tucked. The module 116 may cause the processor 106 to identify a plurality (e.g., a set) of points having a depth characteristic above the bed plane 202. In this implementation, the processor 116 identifies a plurality of points from a first side (e.g., the "top" side or the side of the bed that the patient's head is proximally located) to a second side (e.g., the "bottom" side of the bed or the side of the bed that the patient's feet (or foot, legs, etc.) are proximally located. For example, the module 116 may cause the processor 106 to compute by way of a suitable scan line technique of one or more of the identified points (e.g., body points) representing the patient. For instance, the processor 106 may utilize mean shifted processes or center of mass processes to identify a plurality of points (pixels) representing a portion of the object 204. Thus, the processor 106 can utilize a subset of the points 213 to generate one or more lines 214 (or "trace" a line from the first side of the bed to the second side of the bed) utilizing one or more statistically noise-resistance techniques to determine a general orientation of the patient's body within the bed. The points utilized when generating the lines 214 may be weighted by various criteria so as to provide greater importance to a first pixel as compared to a second pixel. For example, pixels that are determined to be higher above the bed plane 202 as compared to pixels that represent portions of the space that are lower than the bed may be given a greater weight. Thus, the module 116 is configured to cause the lines 214 to represent (move towards or gravitate towards) the segmented points that are higher than the bed.

Figure 2C:
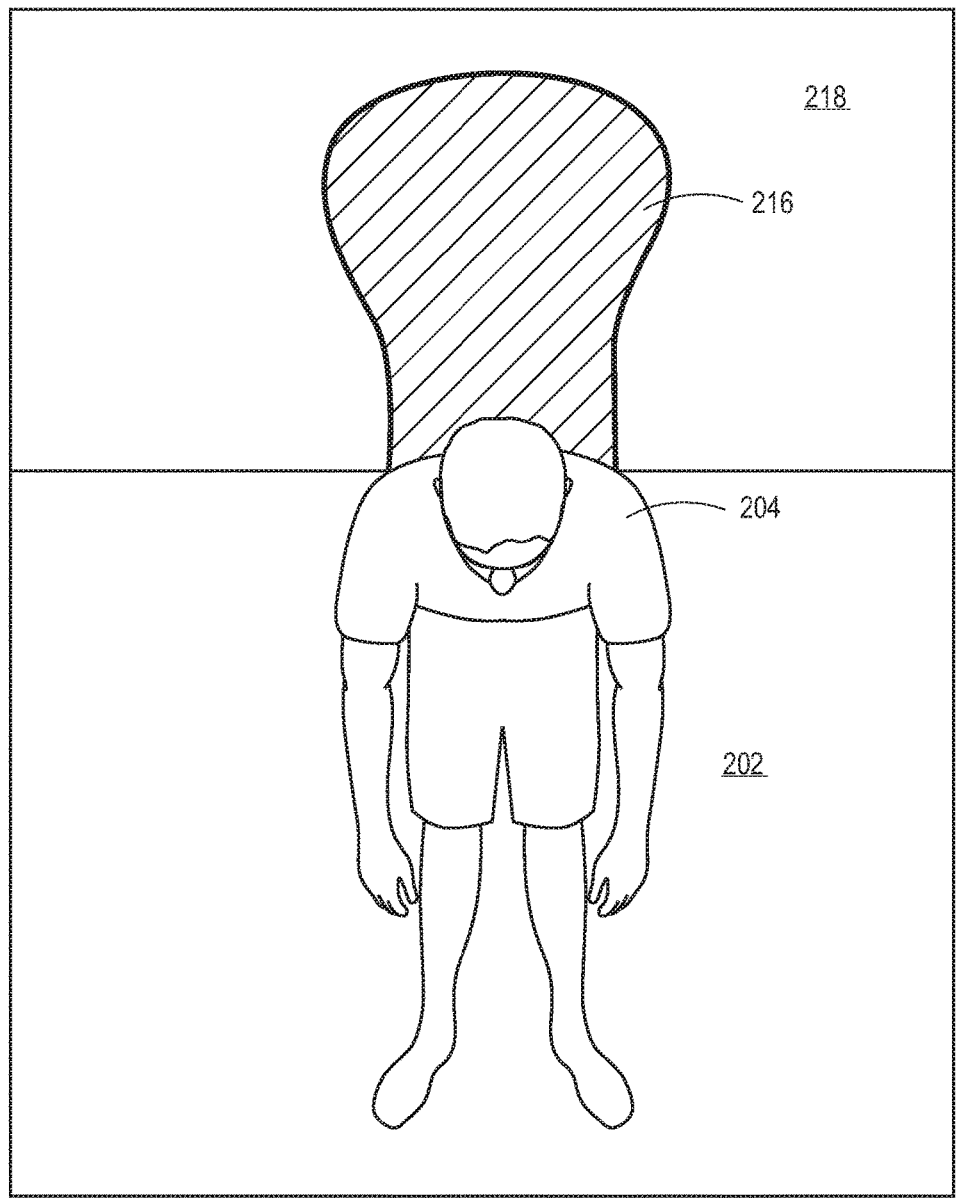

As shown in FIG. 2C, the module 116 may cause the processor 106 to identify whether an object 204 is sitting in the bed. For example, when an object 204, such as a patient, is sitting up in bed, the processor 106 may identify one or more regions 216 identified as having zero pixels within a region 218 of the bed plane 202 (e.g., processor 106 determines there is no depth data associated with the region 218). The processor 106 may also determine that the object 204 is sitting in bed based upon the processor 106 determining that pixels having a depth value classified as representing the body (e.g., pixels having a certain height above the bed) are not identified within the region 218 (e.g., top of the bed). The processor 106 may also determine that the object 204 is sitting based upon an determination that a threshold of pixels classified as representing the body are proximate (e.g., adjacent) to the region 216.

Figure 2D:
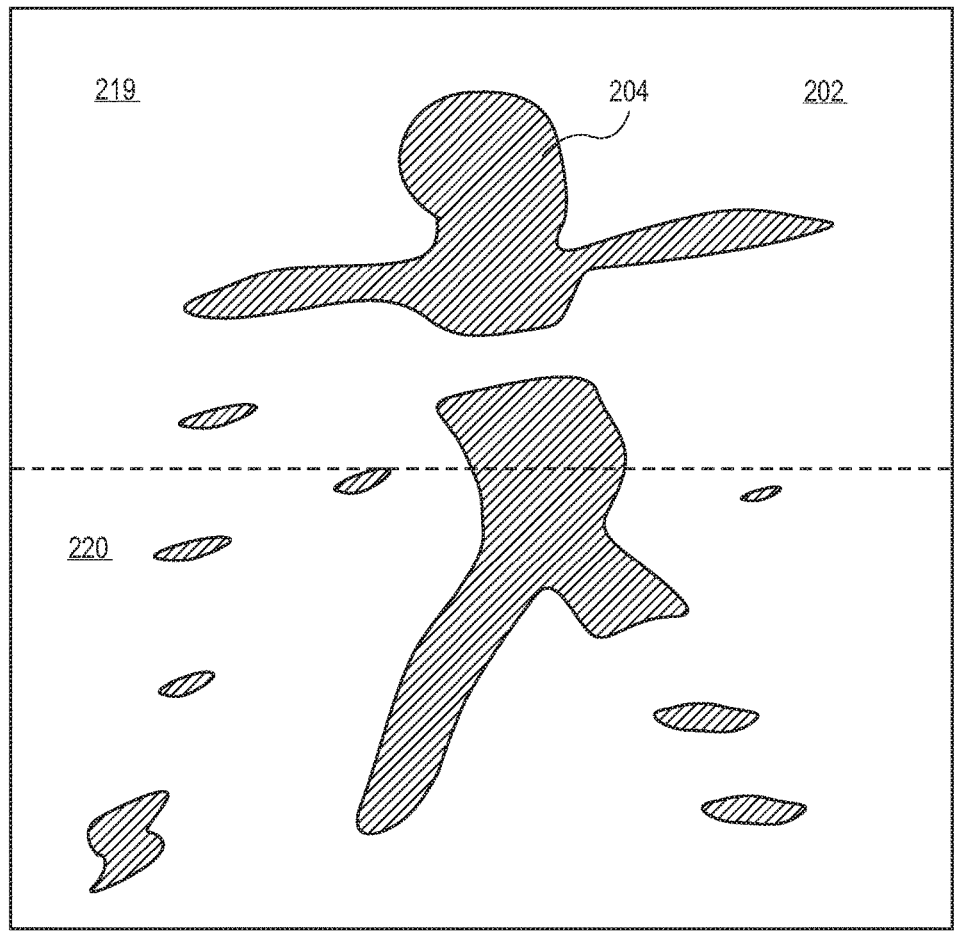
Figure 2E:
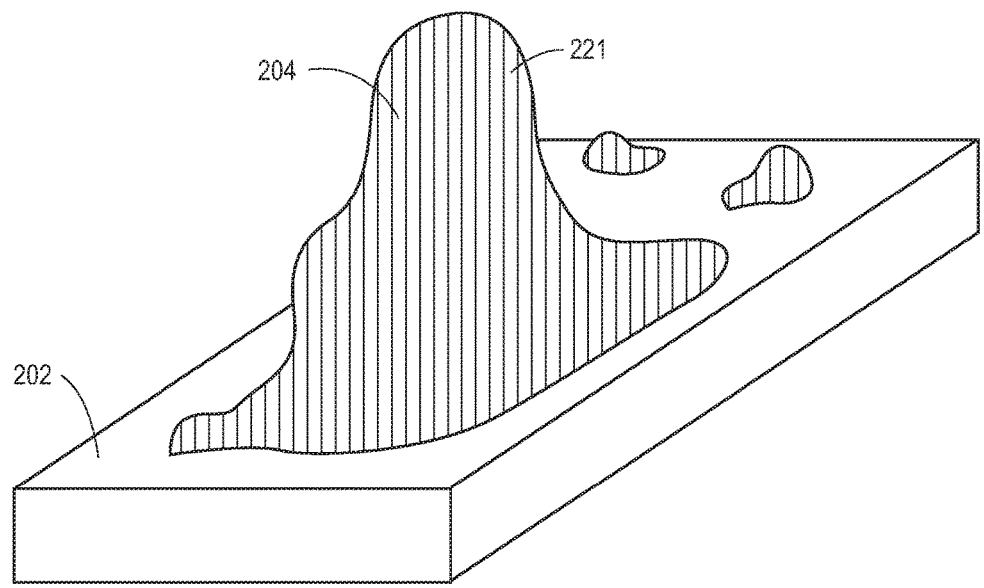

In another implementation, the module 116 may cause the identification, or positioning, of the object 204 through a determination of a relatively uniform distribution of body pixels from the first region 219 of the bed plane 202 to the second region 220 of the bed plane 202 (see FIG. 2D). In another implementation, as shown in FIG. 2E, the processor 106 may identify a mass (e.g., subset) 221 of pixels having depth values above the bed plane 202 (e.g., proximal to the camera 102 as compared to the pixels representing the bed). In an implementation, the subset of pixels may represent a volume or mass above the bed plane 202 that is indicative of the object 204 sitting up. Based upon the subset 221 of the identified pixels, the processor 106 can be instructed by the module 116 to integrate over the subset of pixels to determine an approximate volume between the pixels identified as above the bed and the bed itself. Additionally, one or more clustering techniques may be utilized such that the system 100 is tolerant of other objects located within the bed (e.g., pixels representing other objects having depth values above the bed plane). Thus, a center of mass technique may be utilized to determine whether a center of mass (e.g., pixels) is a certain height above the bed, which is indicative of the patient sitting up.

Figure 2F:
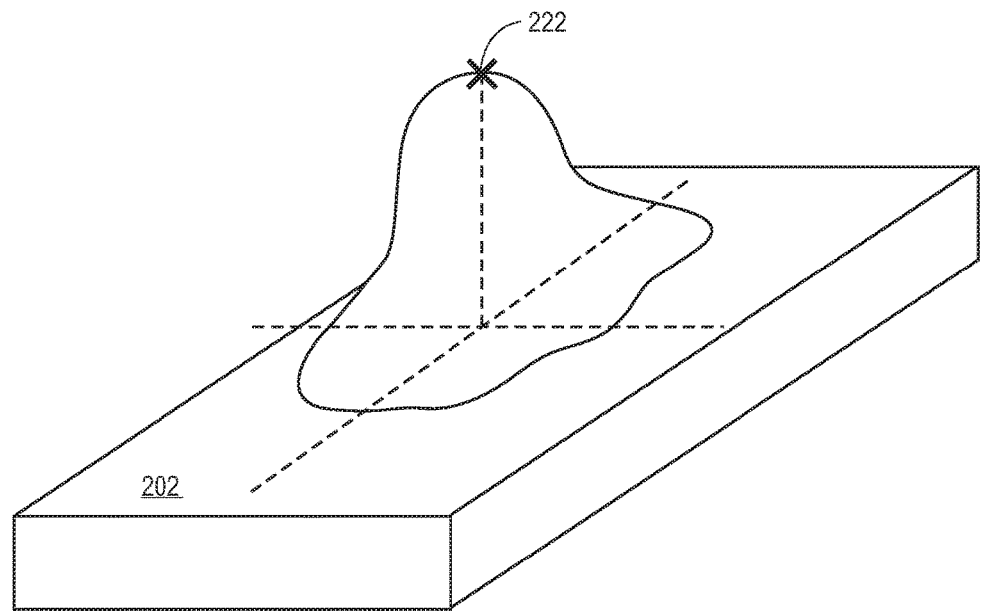

In yet another implementation, the module 116 may cause the processor 106 to analyze and determine which pixel represents the point 222 most distant from the bed plane 202 (e.g., x, y, and z coordinates that, when converted into a distance from pixels representing the bed plane 202, yield a value that is greater than the value calculated for the other pixels identified as representing a discrete object over the bed with respect to pixels representing the bed plane). In this implementation, the most distant pixel may indicate a height (maximum height) of the object above the bed, which may be indicative that the object 204 is sitting up in bed (see FIG. 2F).

Figure 2G:
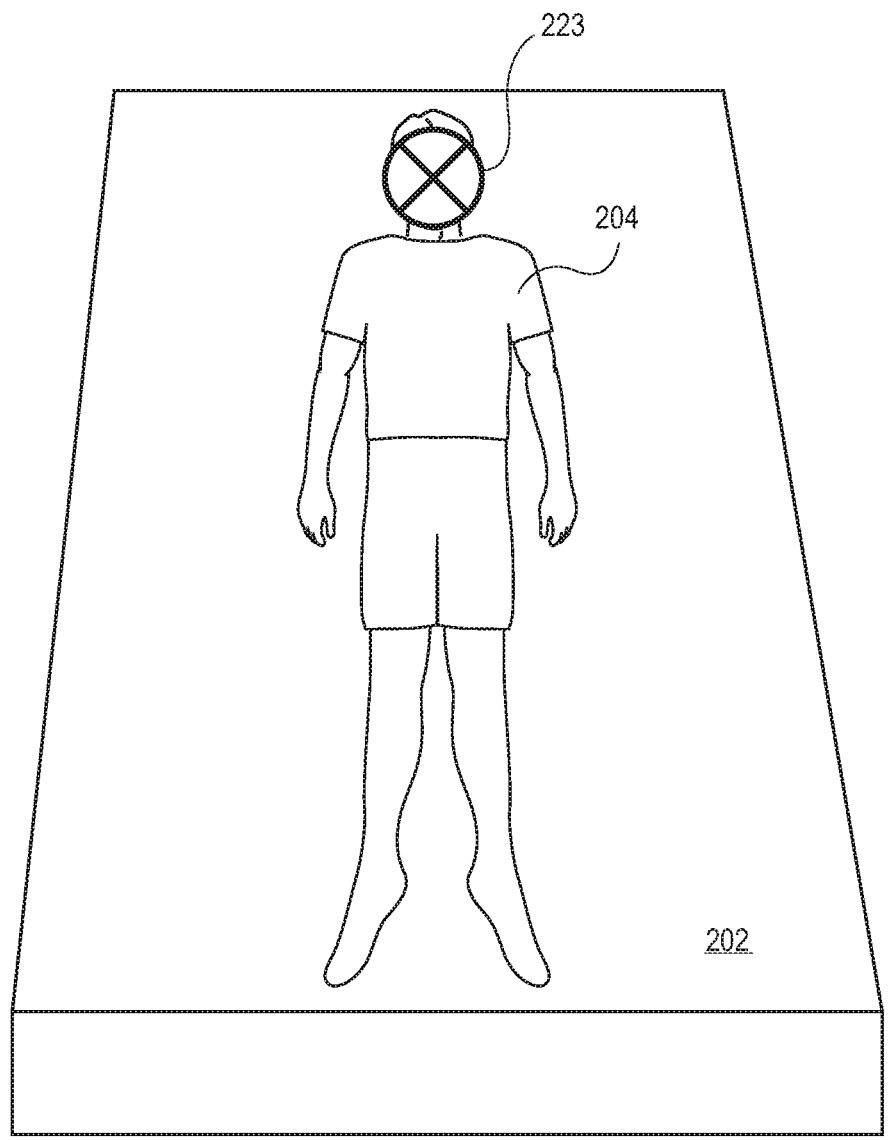

In yet another implementation, as shown in FIG. 2G, the system 100 may incorporate facial detection techniques to determine a body orientation of the patient. In one or more implementations, the system 100, such as the module 116 and the processor 106, may incorporate suitable machine-learning techniques to assist in the detection of pixels 223 representing the face of the patient. Thus, the processor 106, in conjunction with the module 116, can increasingly (e.g., higher accuracy or confidence intervals) determine the body orientation through the classification of individual body parts based upon the facial recognition (e.g., determine pixels representing individual body parts based upon the pixels identified as representing the face). It is contemplated that the system 100 may also utilize the orientation of the bed to indicate, or aid, in determining the body orientation and the body position of the object 204.

Figure 2H:
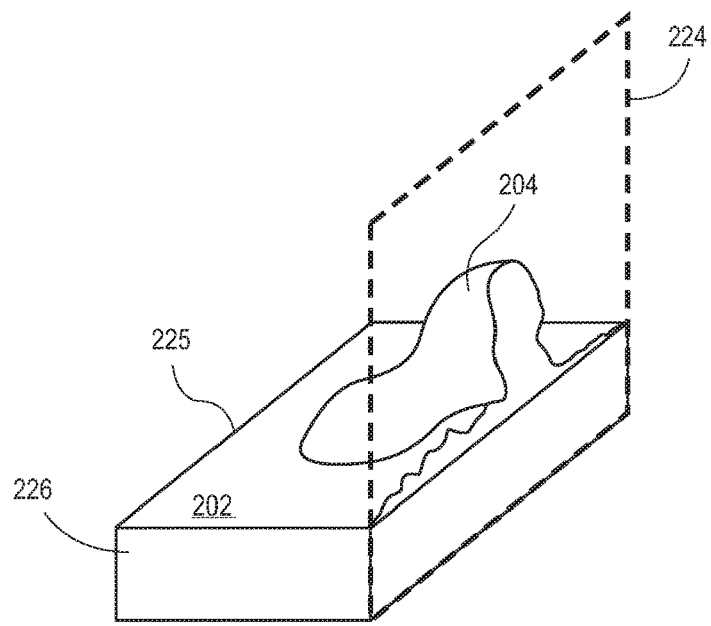

In yet another implementation, the system 100 may identify patients getting out of or getting into the bed. For example, as shown in FIG. 2H, the module 116 causes the processor 106 to define a plane 224 at an edge 225 of the bed 226 such that the processor 106 can identify an object 204 (e.g., a grouping of pixels) that are within the FOV of the camera 102 and are over the bed 226. More specifically, the processor 106 can identify subsets of pixels (a subset of pixels having a predefined number of pixels within the subset) that change (e.g., pixel transitions to representing another object, such as a wall, the bed 226, etc.) within a predefined number of frames (as well as pixels that are connected to the bed [e.g., grouping of pixels having a subset of pixels adjacent to the pixels representing the bed]) to indicate whether the object 204 has transitioned out of or transitioned into the bed 226. By identifying subsets of pixels proximate to the bed 226, the processor 106 can remove people that are reaching over the bed 226 or objects 204 that are within the bed 226 or positioned within the bed 226. For example, the module 116 is configured to cause the processor 106 to determine that the patient is putting an extremity outside of the bed 226 by approximating, utilizing a noise tolerant method, the surface area of objects not above the bed plane 202 of the bed 226. In another example, the module 116 causes the processor 106 to detect an arm reaching out of the bed 226 based upon an identification of a subset of pixels representing the arm that are above the bed plane 202. If the module 116 detects pixels above a predetermined threshold, the module 116 determines that the patient is moving a body part outside of the bed.

Figure 2I:
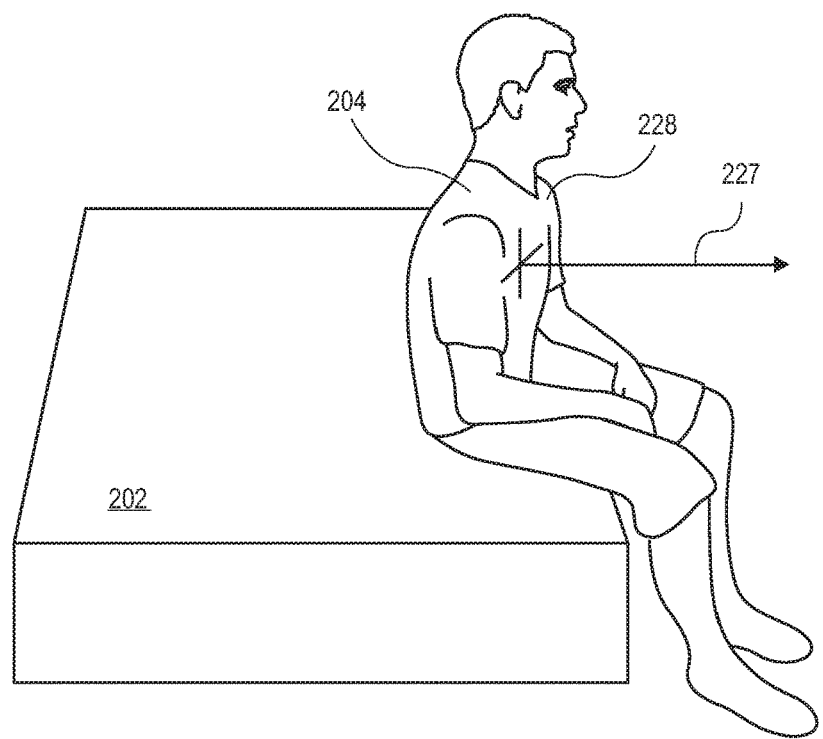

In yet another implementation, the system 100 is configured to analyze one or more component vectors (shown as vector 227) belonging to a subset 228 (e.g., mass) of pixels representing the object 204 to at least partially assist in determining the orientation of the subset of pixels (see FIG. 2I). For example, the module 116 is configured to determine one or more component vectors associated to (e.g., belonging to) a portion the subset 228 of pixels. Based upon the determined component vectors, the module 116 is configured to cause the processor 106 to determine an orientation of the object 204 represented by the subset 228 of pixels. In each of the implementations described above, the module 116 may cause the issuance (e.g., generate and transmit) of an electronic communication indicating the presence of an object (patient) within the bed or whether the object was not determined to be within the bed. In some implementations, the system 100 is configured to interface with third party systems that may issue alerts to medical personnel based upon the electronic communication.

In another implementation of the present disclosure, the patient monitoring module 116 includes a fusion engine 118 for determining a state (e.g., position of the human relative to the bed, the side on which the patient is lying, etc.) associated with the human. The fusion engine 118 may implement one or more algorithms corresponding to sensor fusion techniques that map one or more input signals representing a possible state of the patient to a probability distribution (e.g., a set of weighted parameters) associated with possible output states (e.g., determinations of the state of the patient). In a specific implementation of the present disclosure, the fusion engine 118 may implement a Hidden Markov model for assigning weighted parameters to signals associated with the captured environment (e.g., data signals indicating whether there is motion within the captured environment, signals representing a body part, data signals extracted from the captured image data, etc.). More specifically, the fusion engine 118 is configured to determine and to apply weighted parameters to techniques for capturing data associated with one or more pixels. For example, the fusion engine 118 applies a first weighted parameter to data corresponding to a first technique (e.g., a first signal) and applies a second weighted parameter to data corresponding to a second technique. In this example, the first and the second weighted parameters may be the same or may be different. For instance, the weighted parameter may be applied based upon the body portion, the orientation of the body part, the technique utilized, or the like. Based upon the weighted parameters, the module 116 causes the processor 106 to determine a state of the patient (e.g., the side on which the patient is positioned, patient is positioned on the floor, patient is sitting in bed, etc.).

One or more characteristics 120 may be furnished to the system 100 by a user, such as a caregiver (e.g., medical personnel). The characteristics 120 may include, but are not limited to: age, gender, weight, body type/dimensions, diagnoses, time of day, able-bodied, gait characteristics, mental status, physical restrictions (e.g., missing limbs), facial deformalities, sleeping abnormalities, angle of bed, dimensions of bed, additional equipment in room (e.g., standing IV), fall risk score (e.g., fall risk as determined by the Morse Fall Scale), patient schedule, caregiver has moved the patient, patient ethnicity and/or skin tone, bed characteristics (e.g., pillow/sheet colors/patterns), and/or patient history of side lying activity. In one or more implementations, the system 100 may utilize suitable machine learning techniques to identify (e.g., "learn") one or more characteristics 120 of the patient. For example, the system 100 may identify one or more characteristics 120 of the patient while monitoring the patient over a time period (e.g., determine which side the patient is positioned, determine a tendency of the patient at discrete time periods, etc.).

Figure 2J:
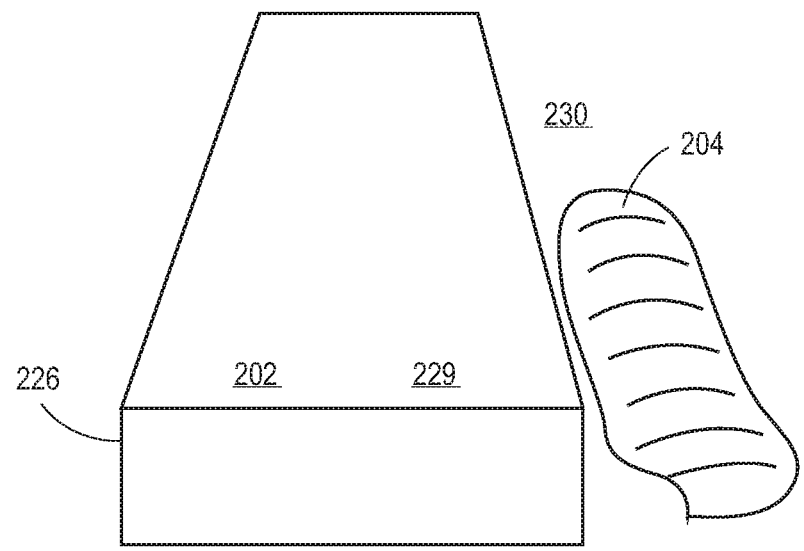

As described in greater detail below and with respect to FIGS. 2J to 2Z, the system 100 is configured to utilize various processing techniques to identify zero or more pixels (or subsets of pixels) representing a body part of an object 204 or pixels associated with a body part (e.g., blanket covering the body, etc.). Each of the processing techniques described below represent a distinct processing technique for identifying a state of the patient (e.g., orientation of the patient within the bed) and may be utilized simultaneously to determine a state of the object 204 (e.g., described hereinafter as patient 204). For example, a first technique (e.g., a first signal) may be utilized to identify one or more pixels representing a body part, and a second technique may be utilized to identify one or more pixels representing another (or the same) body part. The processor 106 utilizes the fusion engine 118 to apply a weighted parameter to each data set associated with each "signal" (e.g., the data associated with the pixels identified through the specified technique). As described above, the fusion engine 118 may utilize a suitable model, such as a Hidden Markov model, to apply the weighted parameters. However, it is understood other suitable models may be utilized. Based upon the weight parameters associated with each data set, the processor 106 determines a state of the patient. In the techniques described above, multiple cameras 102 may be utilized through the environment to provide additional views, or angles, of the environment. In some implementations, the system 100 may apply skeletonization techniques to identified masses to identify movement of the mass within the environment. In some of the implementations described herein, RANSAC techniques, or other geometric shape matching and modeling, may be utilized to identify pixels representing the bed, floor, or other objects within the scene (e.g., for point subtraction). For example, these techniques may be utilized to identify pixels representing rails associated with the bed for template matching, which is described herein.

In yet another implementation, the system 100 is configured to determine whether an object 204 is positioned on the floor (i.e., the patient fell from his or her bed). The module 116 is configured to utilize background subtraction methods to locate objects 204 that are outside of the bed 226. Background subtraction techniques include keeping track of a maximum depth of at least substantially every pixel location (see FIG. 2J). Based upon the maximum depth value, a pixel having a depth value closer than the maximum depth value represents a foreground (represented as region 229, and pixels having a depth value at or below the maximum depth value represents background (represented as region 230). For example, the processor 106 is configured to determine pixels that represent the bed 226 with respect to other objects within the field of view of the camera 102. The surface area of the objects identified as outside of the bed 226 are estimated. The processor 106 determines the object 204 to be a human when the estimation is greater than a defined threshold of pixels (e.g., a subset of pixels is greater than a defined threshold of pixels). The module 116 is configured to instruct the processor 106 to differentiate between a standing person and a person lying down based upon the percentage of pixels representing the object 204 (based upon the surface area) classified as above the bed 226 as compared to the percentage of pixels of the object 204 classified as below the bed 226. For example, if the percentage of the pixels representing object 204 detected below the bed 226 is above a defined threshold (e.g., greater than forty percent, greater than fifty percent, etc.), the module 116 instructs the processor 106 to determine that the person is lying down within the FOV of the camera 102. Thus, the processor 106 is configured to identify a subset of pixels representing a mass proximal to the subset of pixels representing the floor that were not proximal to the floor pixels in previous frames. In this implementation, the module 116 determines that the patient is on the floor when the subset of pixels representing the mass proximal to the subset of pixels representing the floor that were not proximal to the floor pixels in previous frames.

Figure 2K:
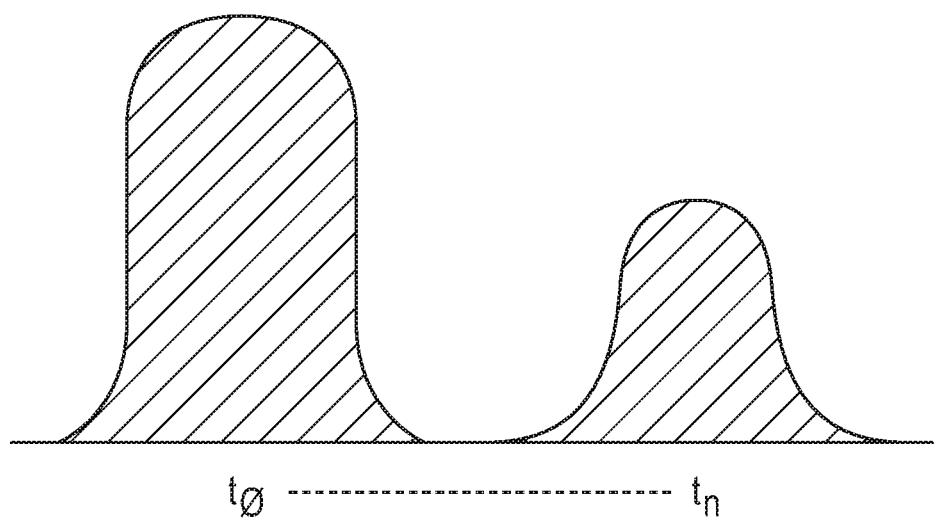

In another example, as shown in FIG. 2K, the module 116 is configured to determine a movement of the object 204 within the bed 226. For example, the module 116 is configured to cause the processor 106 to approximate a total change in volume of the detected pixels representing the object 204 (e.g., patient) in the bed within one image frame to the next image frame (e.g., the change in volume of pixels from $t_0$ to TN). If the total change in volume of the object is above a defined threshold, the module 116 is configured to cause the processor 106 to issue an alert indicating that the patient may not be moving beyond the defined medical protocol. The system 100 is configured to track pixels associated with a mass over a number of depth frame images. If the processor 106 determines that the pixels representing the mass move closer to the floor (e.g., depth values of the pixels representing the mass approach the depth values of the pixels representing the floor), the processor 106 may determine that the object representing the mass is falling to the floor. In some implementations, the system 100 may utilize sound detection (e.g., analysis) in addition to tracking the pixels to determine that the patient has fallen. For example, the processor 106 may determine that a sudden noise in an otherwise quiet environment would indicate that a patient has fallen.

Figure 2L:
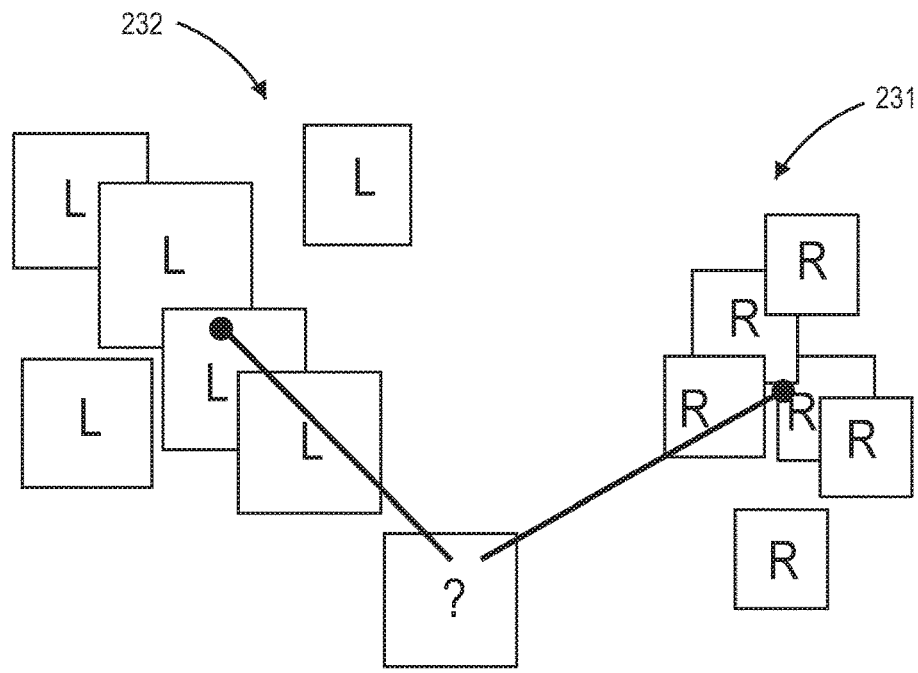
Figure 2M:
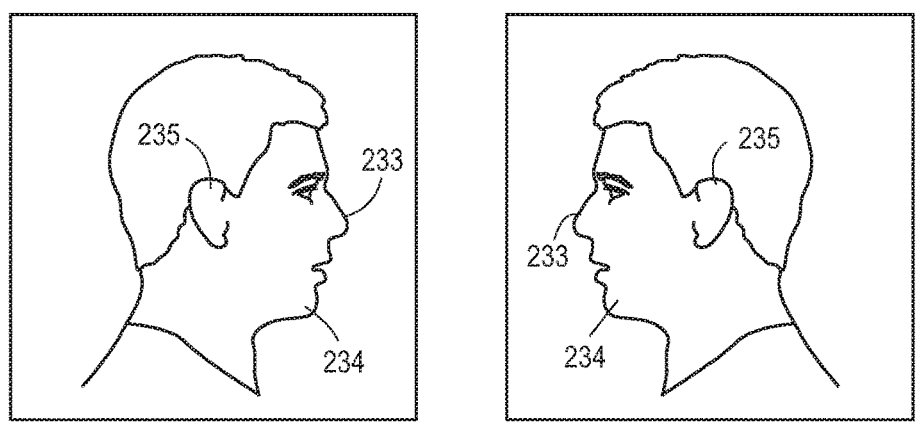

In another implementation, as shown in FIGS. 2L and 2M, the system 100 may receive one or more right-facing images 231 and left-facing images 232 of a patient 204. The system 100 utilizes machine-learning techniques that may include, but are not limited to: cascading Haar classifiers, decision tree algorithms, neural network algorithms, support vector machines, clustering, histogram of gradient techniques, and/or Bayesian network algorithms to generate a parameter utilized for computing a similarity metric between the images (e.g., a distance parameter, locations of specific identified features, and/or measure of confidence that a given subset of pixels represents a specific feature). The module 116 causes the processor 106 to process one or more depth frame images and apply the distance parameter (e.g., similarity metric) to pixels identified as representing one or more facial characteristics. Based upon the application of the parameter and/or the metric, the processor 106 generates a signal representing a possible orientation of the patient (e.g., the side on which the patient is lying).

The module 116 may utilize machine learning techniques (e.g., utilizes a machine learning classifier) to cause the processor 106 to determine a subset of pixels that the processor 106 determines most likely to represent the body and/or the face of the patient. The processor 106 is also configured to output a confidence parameter (e.g., a value ranging between 0 and 1) representing the confidence that the subset of pixels identified is the body and/or the face. In another implementation, the module 116 is configured to cause reporting of an orientation of the body or face (for example, via a degree of rotation, where −90 degrees represents the patient facing left, 0 degrees represents the patient facing up, 90 degrees means facing right, etc.) and a confidence parameter associated with that orientation. The confidence parameter is based on how similar the current situation is to situations that the machine learned classifier has encountered before, as measured by a similarity metric.

Figure 2N:
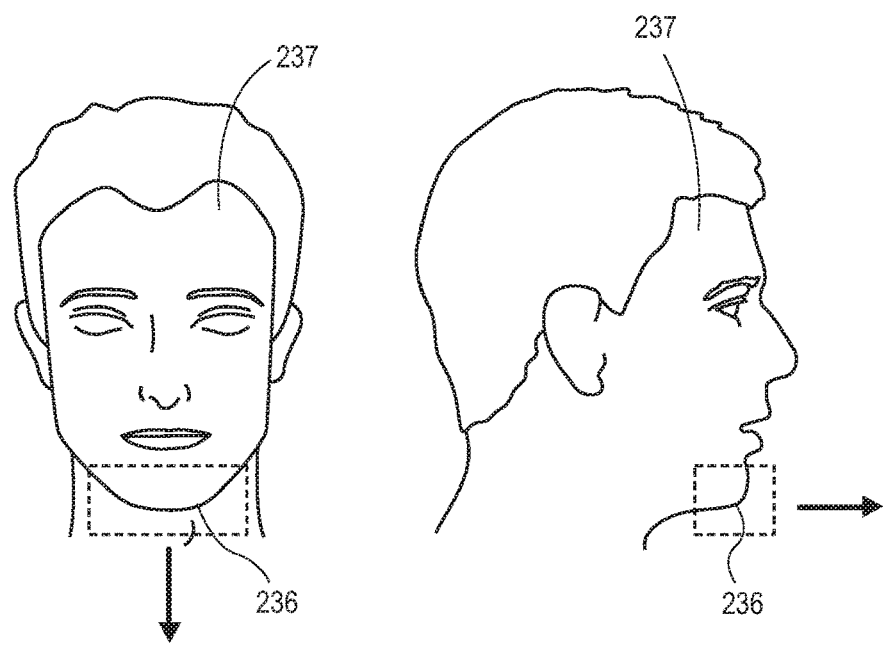

As shown in FIG. 2M, the module 116 is configured to cause the processor 106 to identify a subset 233 of pixels as representing one or more facial characteristics of the patient. For example, the processor 106 is configured to determine whether the face is right-facing or left-facing with respect to the camera 102 based upon the orientation of the pixels representing the one or more facial characteristics. The module 116 may cause the processor 106 to identify one or more pixels representing facial characteristics (e.g., direction of the pixels representing the nose 233, direction of the pixels representing the chin 234, characteristics of the pixels representing the ears 235, etc.) utilizing a feature recognition technique, such as a Haar recognition technique. Based upon the orientation of the identified pixels of the facial characteristics, the processor 106 is configured to determine a state of the patient. For instance, the state of the patient may be positioned on the patient's right side with respect to the camera 102, positioned on the patient's left side with respect to the camera 102, or positioned on the patient's back. In some implementations, the processor 106 is configured to cross-reference the characteristics 120 with the identified pixels of the facial characteristics to determine an orientation of the facial characteristics with respect to the camera 102. For example, the fusion engine 118 may utilize one or more of the characteristics 120 to assist the processor 106 in determining the orientation of the facial characteristics with respect to the camera 102. In a specific implementation, as shown in FIG. 2N, the system 100 is configured to identify one or more pixels as representing a chin 236 of the patient. For example, the module 116 causes the processor 106 to identify pixels as representing a chin of the patient. Based upon the orientation/direction of the chin, the processor 106 generates a signal representing a possible directionality (e.g., orientation) of the head 237, which is utilized to determine a state of the patient (e.g., the side on which the patient is lying).

Figure 2O:
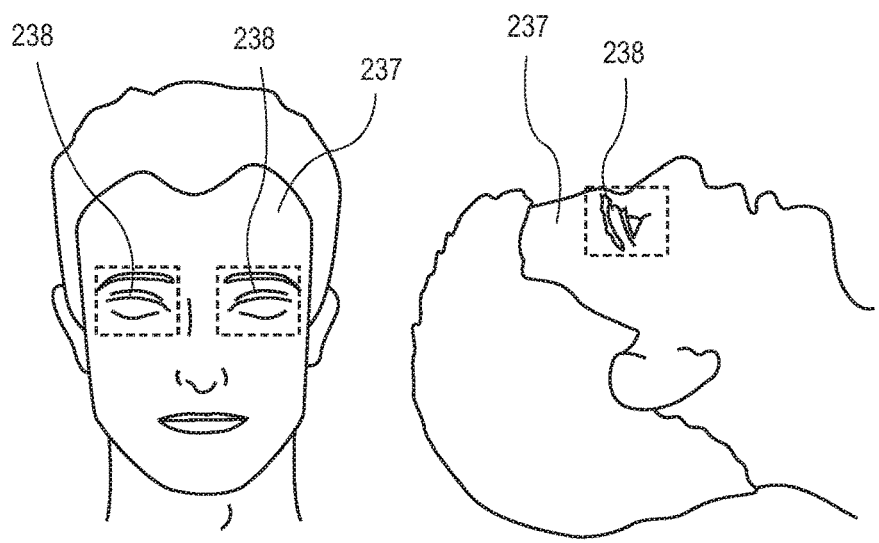

As shown in FIG. 2O, the system 100 is configured to identify pixels representing an eye socket 238 (or eye sockets) of the patient. In an implementation, the module 116 is configured to cause the processor 106 to identify the eye socket(s) based upon RGB values (e.g., signals such as hue, shading, color, etc.) of the pixels representing the eye sockets as compared to the depth values of the pixels representing the surround regions of the face of the patient. Based upon the identified pixels, the processor 106 is configured to determine the orientation (direction) of the head 237 of the patient. Thus, this orientation comprises one of the signals (e.g., signal represents the determined orientation) that is used, in conjunction with other signals, to determine a probability distribution of the possible states of the patient.

Figure 2P:
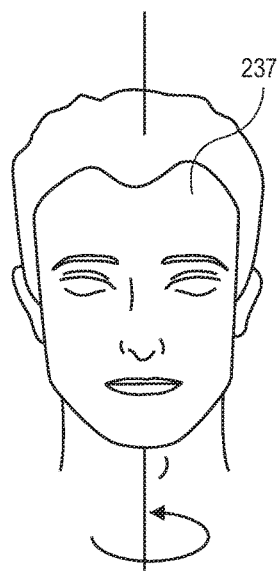

As shown in FIG. 2P, the system 100 is configured to generate a distance metric for various orientations of the patient's head 237. For example, over a time interval, the system 100 monitors a patient. The processor 106 is configured to measure between at least two pixels representing distinct regions of the patient's head (e.g., pixels representing ear and pixels representing chin, pixels representing eye, pixels representing mouth, pixels representing nose and pixels representing mouth, pixels representing nose and pixels representing chin, pixels representing ear and pixels representing mouth, etc.) and generate at least one distance metric relating to the distinct regions. In some examples, patient photos may be utilized by the system 100 as "seed" data (e.g., initial data provided to the system 100 utilized as a template). The processor 106 is configured to utilize this distance metric as training data to generate a virtual rotation of possible orientations of the head. Thus, the processor 106 generates a set of distance metrics corresponding to one or more potential orientations of the patient's head (e.g., generate a distance metric for each orientation of the patient's head). Based upon the depth frame images, the processor 106 processes the depth frame images to identify pixels representing one or more facial characteristics. The processor 106 applies the distance metric to the identified pixels to generate a signal representing a possible orientation of the patient's head.

Figure 2Q:
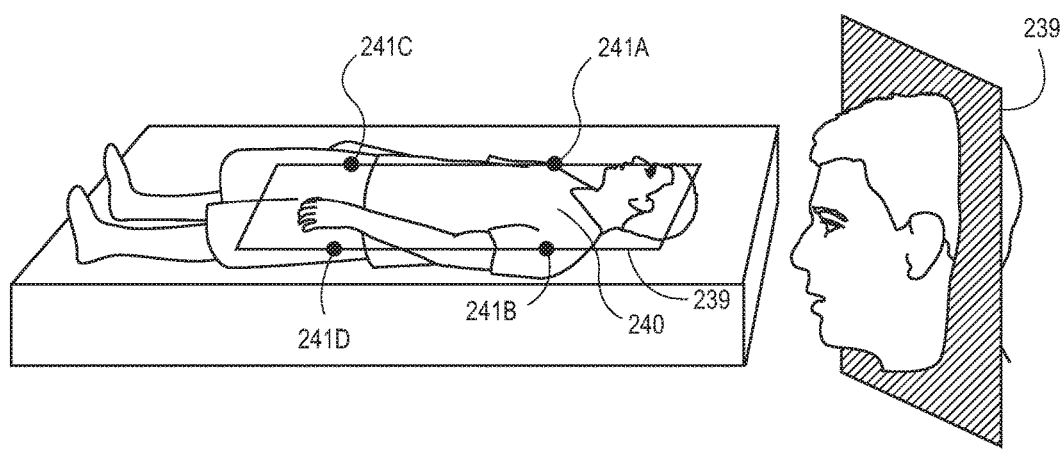

As shown in FIG. 2Q, the processor 106 is configured to apply a plane 239 (e.g., identifying a geometric equation for a plane where depth values that satisfy the equation approximately match depth values of pixels within) to the upper torso region 240 of the patient's body approximating the coronal plane (e.g., shoulder and hip points 241A through 241D) utilizing a color or a depth frame image. For example, the processor 106 identifies pixels from a depth frame image corresponding to two or more regions (e.g., shoulders and hips, etc.) of the patient's torso. The processor 106 is configured to identify pixels corresponding to facial characteristics situated to one side of the coronal plane or the other. If the processor 106 determines that a first threshold of the pixels representing the head's mass (e.g., nose, chin, ears) are on a given side of the plane 239, the processor 106 determines that the side on which the patient is lying is the patient's left side or right side as appropriate. Thus, based upon the number of pixels representing the head identified and their position relative to the plane, the processor 106 is configured to generate a signal representing a possible state of the patient.

Figure 2R:
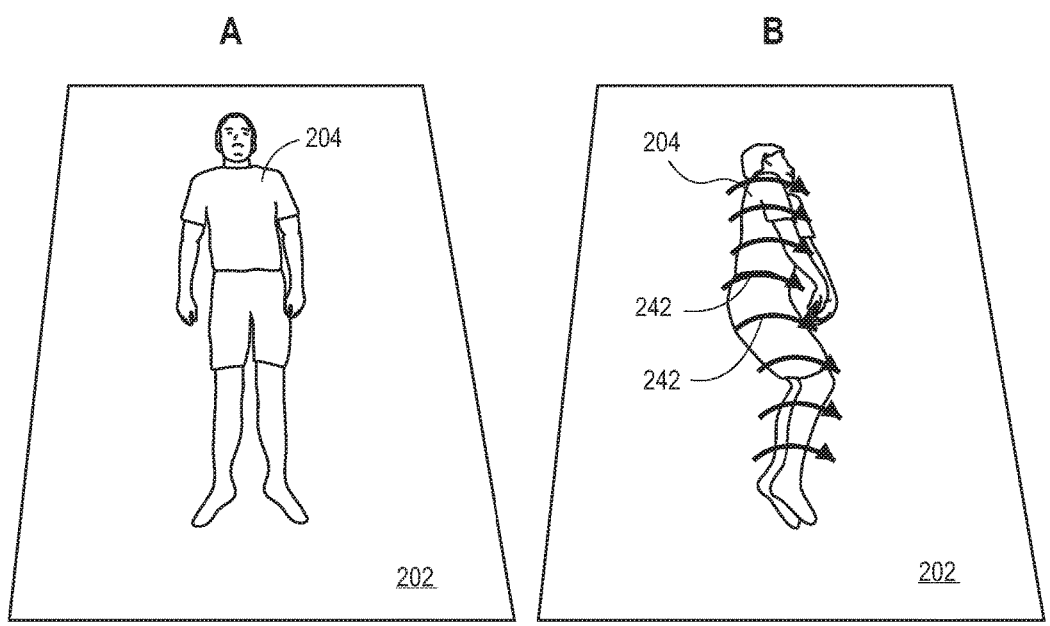

The module 116 is configured to cause the processor 106 to track a direction of rotation of the patient's body. For example, as shown in FIG. 2R, the processor 106 may identify one or more pixels representing the patient 204 to track (see FIG. 2R "A"). Thus, the processor 106 is configured to track a point (e.g., a pixel) through successive depth frame images, which would represent a direction vector 242 or direction vectors 242 over a set amount of time (e.g., processor 106 generates one or more direction vectors 242 based upon the tracked points). The processor 106 can identify an average direction of the motion based upon the tracked point through successive depth frame images aggregating information from each pixel to generate a signal representing a possible side on which the patient is lying (see FIG. 2R "B"). The processor 106 can then use this information to determine if the patient is changing between states (e.g. the patient is turning from their left side to facing forward, or from their right side to lying on their stomach, or from lying down to sitting up).

Figure 2S:
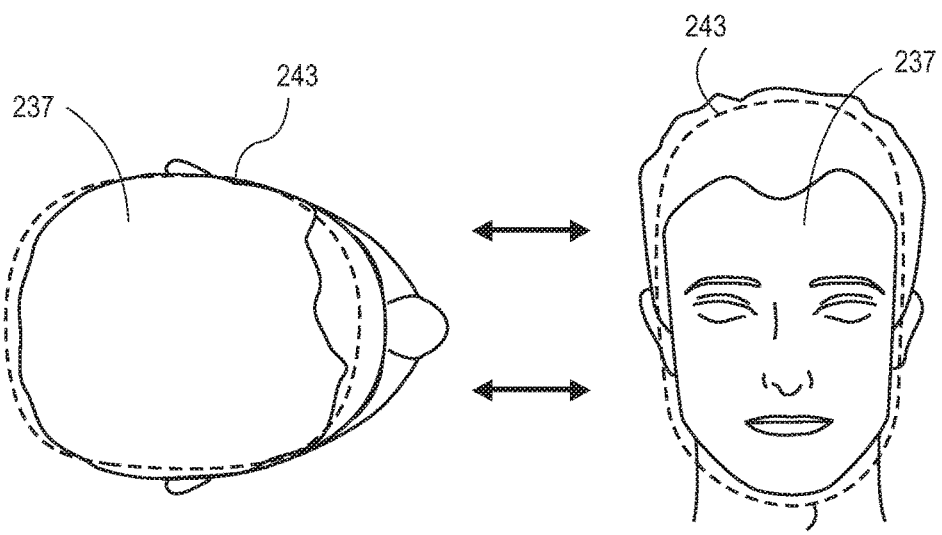

In an implementation, the module 116 causes the processor 106 to track pixels representing the head 237 of the patient (see FIG. 2S). In a specific implementation, the module 116 causes the processor 106 to identify pixels approximately matching a geometric template 243 (e.g., an ellipsoid). For instance, the geometric template 243 may be preprogrammed within the system 100 to provide the system 100 a baseline for identifying pixels representing a body part of the patient. In other words, the geometric template may be a characteristic 120. Thus, the system 100 may include one or more geometric templates 243 corresponding to one or more body parts. In some implementations, the processor 106 identifies a subset of pixels (e.g., a window of pixels) and determines whether a number of pixels within the subset of pixels approximately match the geometric template 243. In order to identify the pixels representing the body part, the module 116 may cause to the processor 106 to utilize a suitable matching algorithm that translates (e.g., rotates) the geometric template 243 to approximately match the template to the pixels representing the body part. This could for example be used to determine orientation of the body part. Based upon a matching geometric template, the processor 106 is configured to generate a signal representing a possible state of the patient.

Figure 2T:
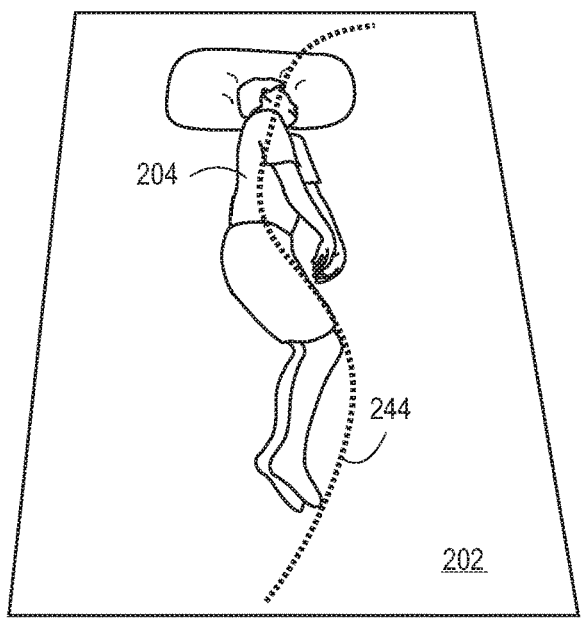

In another implementation of the present disclosure, the module 116 causes the processor 106 to identify a cluster of pixels (e.g., a clustering of pixels) above the bed plane 202 to determine a body position within the bed. For example, the module 116 may utilize one or more sampling techniques that are tolerant to a certain amount of noise (e.g., wrinkles in the bed sheet, etc.). For example, the processor 106 is configured to construct a model utilizing data representing the bed based upon one or more depth/color frame images. The processor 106 then removes (e.g., subtracts) the data representing the bed such that the remaining data represents the body (or is associated with the body). In another example, suitable geometric analysis or machine learned feature extractions may be utilized. Thus, the processor 106 identifies a number of pixels having a depth value above the bed to determine a state (e.g., orientation, body shape, etc.) of the patient within the bed. For example, if the processor 106 identifies a number of pixels forming a characteristic "S" shape 244 (see FIG. 2T), the processor 106 determines that the patient is on his or her side (since patient probably could not form an "S" shape while on the patient's back). Additionally, the shape may be utilized to determine the side on which the patient is lying. For example, the processor 106 may cross-reference the identified shape with characteristics 120 to generate a signal representing a possible state of the patient.

Figure 2U:
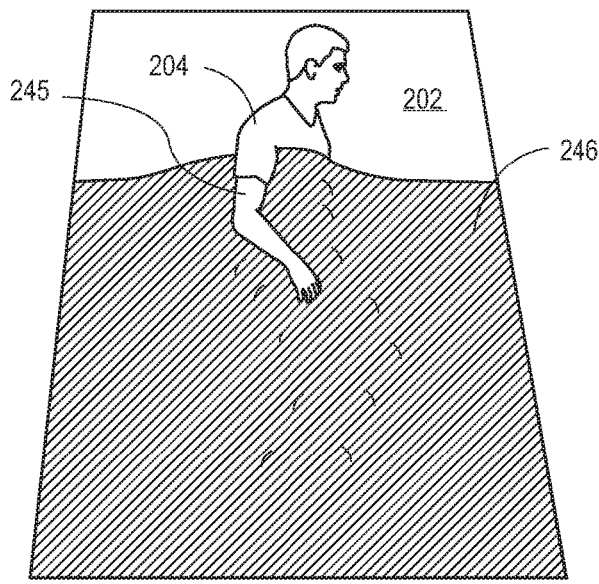

As shown in FIG. 2U, the module 116 is configured to cause the processor 106 to identify pixels representing an arm 245 of the patient 204. The processor 106 may identify pixels representing the arms 245 (e.g., having a depth value proximal to camera 102 as compared to the depth value of the pixels representing the bed plane 204 and/or blankets 246 and/or having a color value distinct from the color value of the blankets). In an implementation, the processor 106 determines the state of the patient based upon the orientation of the pixels representing the arms 245 (e.g., an arm is jointed and can only be angled in certain directions). Thus, the processor 106 is configured to cross-reference the pixels representing the arms 245 (e.g., orientation of the arm) to generate a signal representing a possible state of the patient (e.g., the side on which the patient is lying).

Figure 2V:
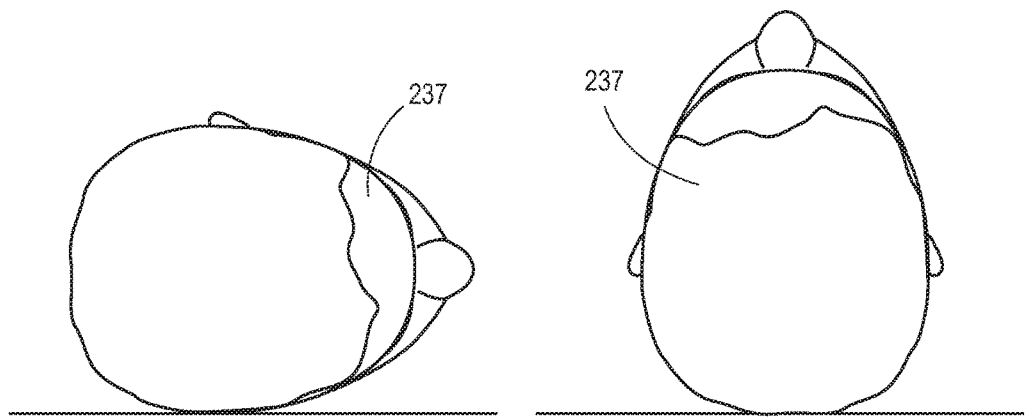

As described above, the processor 106 is configured to identify one or more pixels representing the patient's head 237 (see FIGS. 2N, 2O, and 2V). Upon identifying the pixels representing the patient's head 237, the module 116 causes the processor 106 to generate a signal representing a possible state (e.g., orientation of the head) based upon the contour of the pixels. For example, the processor 106 may identify the contour of the head based upon the pixels representing one or more facial features of the patient (e.g., pixels representing the chin, pixels representing the eye sockets, pixels representing the nose, etc.).

Figure 2W:
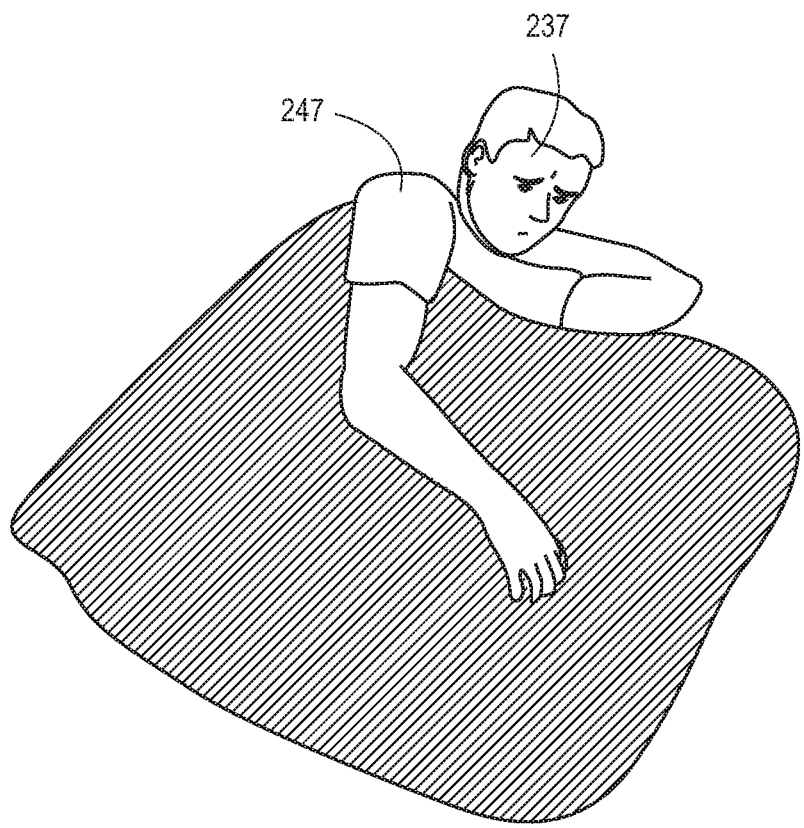

In an implementation, as shown in FIG. 2W, the processor 106 is configured to determine a state of the patient 204 (e.g., the side on which the patient is lying) based upon the depth values of the pixels of the shoulders 247 as compared to the depth values of the pixels of the head 237. For example, if the patient is positioned on the patient's back, the processor 106 may compare the depth values of the pixels representing the head 237 and the pixels representing the shoulders 247. If the depth values of the pixels representing the shoulder 247 are at or below the depth values of the pixels representing the head 237 (with respect to the pixels representing the bed plane 202), the processor 106 determines the patient is positioned on his or her back. If the depth values of the pixels representing the shoulder 247 are above the depth values of the pixels representing the head 237, the processor 106 generates a signal representing a possible state of the patient (e.g., the side on which the patient is lying).

Figure 2X:
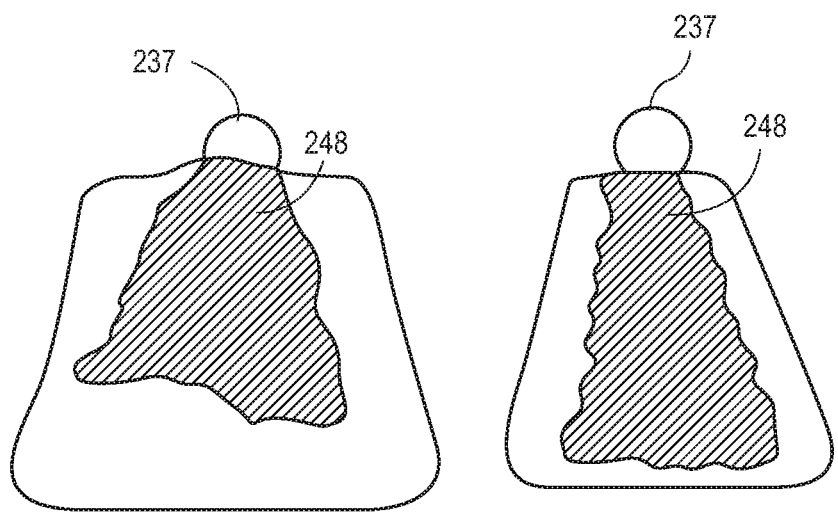

In another implementation, as shown in FIG. 2X, the module 116 is configured to cause the processor 106 to identify and to monitor a length of a number (e.g., a subset 248 of pixels) of pixels having a depth value "above" the bed (e.g., a subset 248 of pixels closer to the camera 102 as compared to the pixels representing the bed plane 202). In one or more implementations, the characteristics 120 may include a length parameter indicating a length of the person and/or sheets when the person is in an extended position (e.g., positioned on the patient's back). When the patient is positioned on his or her side, the patient's feet may be closer to the patient's head to represent a non-extended position. The processor 106 is configured to compare the length of the subset 248 of pixels with the length parameter to generate a signal representing a possible state of the patient (e.g., whether the patient is in the extended position (e.g., supine or prone position) or the patient is positioned in a non-extended position (positioned on the patient's side).

Figure 2Y:
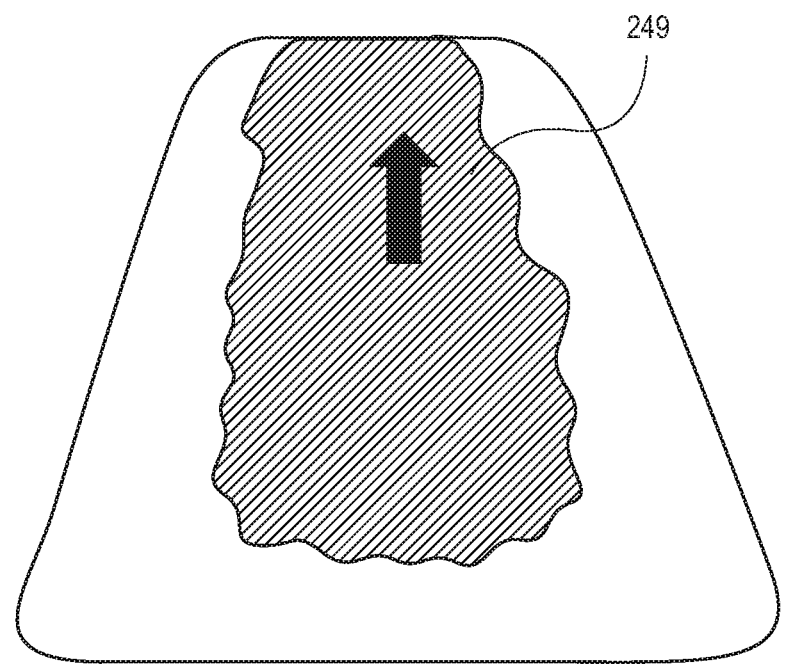

In some implementations, as shown in FIG. 2Y, the module 116 causes the processor 106 to monitor the pixels over a time period to identify moving pixels (e.g., moving points). In one or more implementations, the system 100 monitors the physical environment over an extended period of time to compensate for camera noise and/or other disturbances within the FOV of the camera 102. Thus, the processor 106 may be configured to identify a subset 249 of moving pixels (e.g., pixels having varying depth values from one or more depth frame images) that represent breathing (e.g., arrow represents the subset 249 of moving pixels). Based upon the monitored moving pixel characteristics, the processor 106 is configured to generate a signal representing a possible state of the patient (e.g., that the patient is on the patient's back).

In an implementation, the patient monitoring module 116 can cause the processor 106 to issue an electronic communication based upon one or more states described above or based upon an identification of an action (e.g., gesture) performed by the object 204. For example, the patient monitoring module 116 may represent functionality to cause the processor 106 to identify a gesture performed by the patient. For instance, based upon one or more monitoring techniques described above, the module 116 causes the processor 106 to determine a gesture has been performed based upon an identification of pixels representing a specific body part (e.g., an arm) and to detect movement of the pixels representing the specific body part. The system 100 is configured to track the movement of the identified pixels to determine if the identified pixels correspond to a predetermined movement (e.g., predefined pattern). If the movement matches (e.g., approximately matches) a predetermined movement, the module 116 causes the processor 106 to determine a gesture has been performed (e.g., waving of an arm, movement of a leg, etc.). For example, the processor 106 compares the detected movement to preprogrammed parameters to determine whether the movement is a gesture. Based upon a gesture, the processor 106 issues (e.g., generates and causes transmission) an electronic communication. The electronic communication may be transmitted to medical personnel to indicate that the patient is requesting medical personnel.

The system 100 may also be configured to cause issuance of an electronic communication based upon relative activity of a specific patient. In an implementation, the characteristics 120 may further include data and/or parameters (e.g., activity thresholds) relating to a specific patient's activity (e.g., activity baselines) during specific time periods (e.g., day time, night time). As described above, the module 116 includes functionality to identify pixels representing an object 204 and/or specific body parts associated with the object 204. The module 116 also includes functionality to track activity levels during time periods and compare the tracked activity levels with the characteristics 120. For example, based upon one or more of identified subsets of pixels associated with the object (e.g., head, torso, legs, blanket, arms, etc.), the module 116 causes the processor 106 to track the identified subset of pixels over a discrete time period. As described above, the processor 106 can also track movement (or non-movement) of the object 204. The processor 106 compares data representing the tracked movement (or non-movement) to the characteristics 120, the processor 106 determines an activity parameter during the discrete time period. If the activity parameter is outside the activity threshold, the processor 106 is configured to issue an electronic communication to medical personnel regarding the activity of the object 204.

In some implementations, as shown in FIG. 2Z, the system 100 is configured to track other objects 250 within the FOV of the camera 102. For example, the objects 250 may be medical personnel or the objects 250 may be equipment (e.g., medical equipment) within the patient's room. In one or more implementations, the module 116 is configured to cause tracking of medical personnel to ensure medical personnel are monitoring the patient. For example, the module 116 may cause the processor 106 to identify another subset of pixels as representing an object 250 according to one or more of the techniques described above. In some instances, the processor 106 identifies a subset of pixels representing medical personnel (e.g., a nurse, a doctor, etc.) and determines a time parameter based upon how long the medical personnel were in the FOV of the camera 102 and when the medical personnel entered (and exited) the FOV. The time parameter may indicate whether the medical personnel interacted with the patient or whether the medical personnel simply observed the patient. In some implementations, the system 100 may furnish the time parameters to properly credentialed personnel. These personnel may utilize the time parameters to ensure that the medical personnel monitored the patient during one or more time periods.

The module 116 may include functionality to utilize time parameters to modify alert thresholds associated with the patient. For example, as described above, one or more electronic communications may be issued based upon a state of the patient. These electronic communications may also be based upon an alert threshold. For example, the module 116 may cause issuance of an electronic communication when it has been determined that the patient has moved too much or is transitioning out of the bed. In some instances, a patient may be prone to engaging in unauthorized activity after a medical personnel visit. Thus, in an implementation, an alert threshold may be increased after medical personnel have exited the FOV. In another implementation, the alert threshold may be decreased before a scheduled visit of the medical personnel.

The module 116 may also have functionality to determine whether medical equipment in the patient's room is in the proper location (e.g., position). In some implementations, as described above, the objects 250 may represent medical equipment or other objects within the patient's room. For example, the objects may comprise tray tables, respiratory ventilators, medical furniture, intravenous (IV) equipment, and the like. The module 116 may include functionality to ensure proper location of the objects 250 within the FOV of the camera 102. For example, the module 116 may cause the processor 106 to identify pixels representing one or more objects 250 and determine a position of the objects 250 within the FOV of the camera 102. The processor 106 cross-references the determined position of the object 250 with an object 250 position parameter that indicates where the object 250 should be positioned. If the object 250 is not positioned correctly, the processor 106 issues an electronic communication indicating that the object 250 is not positioned correctly. In some implementations, the objects 250 may comprise bed rails, and the system 100 is configured to determine whether the bed rails are in an upward position or a downward position. The system 100 may compare the values of the pixels representing the bed rails between frames over a discrete time period to determine whether the bed rails have transitioned positions. The system 100 may also compare the values of the pixels representing the bed rails to the values of the pixels representing another object or subject between frames over a discrete time period to determine a configuration of the bed rails.

The module 116 may also include functionality to ensure medical equipment is properly functioning. As disclosed above, the module 116 includes functionality to identify pixels representing a patient's extremities and to determine whether the extremities are moving. The module 116 may also cause the processor 106 to determine whether equipment attached to the patient is functioning properly. For example, the patient may be utilizing a continuous passive motion (CPM) device for knee joint recovery. Based upon the detected motion of the patient's leg, the processor 106 may be configured to determine whether the CPM device is properly flexing and/or extending the patient's knee.

The module 116 also includes functionality to determine whether the patient is not properly positioned. For example, the module 116 is configured to cause the processor 106 to determine whether the patient is entangled within the bed (e.g., leg stuck in rail) or in an orientation that is deemed unsafe. In an implementation, the processor 106 is configured to compare (e.g., cross-reference) pixels representing one or more portions (e.g., extremities) of the patient with pixels representing one or more objects (e.g., bed rails, edge of the bed, etc.). Based upon the cross-reference, the processor 106 may determine the patient is in an unsafe orientation based upon the positioning of the pixels representing the patient's extremities with respect to the pixels representing the one or more objects (e.g., bed rails, edge of bed, etc.). When a determination is made that the patient is in an unsafe orientation, the module 116 causes the processor 106 to issue an electronic communication to alert medical personnel.

In one or more implementations, the system 100 is configured to determine whether the patient is attempting to leave the bed by way of the head of the bed or the foot of the bed. For instance, the module 116 causes the processor 106 to identify pixels representing a head of the bed and/or a foot of the bed. This identification may be accomplished through one or more of the techniques described above. The module 116 also causes the processor 106 to monitor pixels representing the patient (or a portion of the patient) over a time period. If the pixels representing the patient interface with the pixels representing the head of the bed or the foot of the bed (e.g., pixels representing the patient have approximately the same depth value as pixels representing head/foot of the bed), the processor 106 determines the patient is attempting to transition from the bed via the head/foot of the bed. In one or more implementations, the module 116 causes the processor 106 to issue an electronic communication to alert medical personnel in response to this determination.

In one or more implementations, an infrared light source may be utilized to further illuminate the environment to allow the camera 102 to operate within a darkened environment such that the processor 106 can generate one or more signals as described above in the various implementations described above.

Example Monitoring Process

Figure 3:
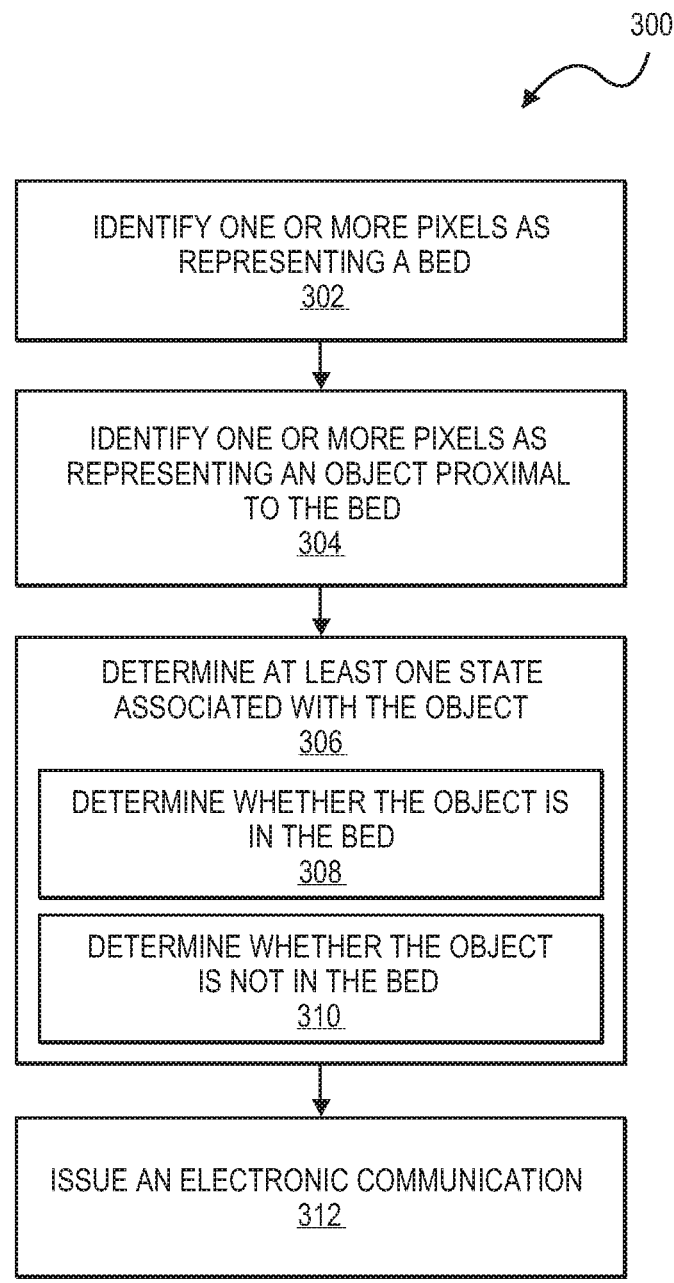
FIG. 3 is a flow diagram illustrating an example method for monitoring a medical environment in accordance with the present disclosure.

FIG. 3 illustrates an example process 300 for determining whether a patient is positioned proximate to a bed utilizing an image capture system, such as the image capture system 100 described above. As shown in FIG. 3, one or more pixels are identified as representing a bed (Block 302). As described above, the cameras 102 are configured to capture image data representing one or more frames within a FOV of the cameras 102 (e.g., data representing one or more color frame images, data representing one or more depth frame images). Once captured, the data is furnished to the computing device 104 to allow the module 116 to cause the classification of whether the pixels represent a portion of a bed. This may be accomplished over one or more frames. Once pixels representing the bed are identified, one or more pixels representing an object (i.e., a human, such as the patient) proximal to the bed are identified (Block 304). For example, based upon the depth data associated with each pixel, a grouping of pixels can be identified as representing an object within the bed. For instance, the module 116 may cause the processor 106 to identify one or more pixels as representing an object within the bed based upon the depth data (comparing a pixel's depth value to another pixel's depth value that represents the bed).

As shown in FIG. 3, at least one state associated with the object is determined (Block 306). The state may be defined as whether the patient is still within the bed, whether the patient is positioned to one side of the bed, whether the patient is positioned on the floor (i.e., the patient is not in bed), whether the patient appears to be getting out of bed, and so forth. For example, a determination is made whether the object is within the bed (or within an acceptable range within the bed) (Block 308). In an implementation, an orientation, such as a positional orientation, of the object (e.g., the patient) within the bed can be determined utilizing the identified object pixels. This may allow for the system 100 to furnish proactive alerts to medical personnel that the patient is taking actions that are not desired (e.g., sitting up, getting up, moving to the edge of the bed, etc.). In another example, a determination of whether the object is not within the bed (Block 310). For instance, the system 100 is configured to determine, as described above, whether the patient is positioned over the floor. In one or more implementations, an electronic communication (e.g., e-mail, SMS text, MMS text, proprietary messaging services [e.g., HL7 messaging], etc.) is issued (e.g., generate and/or transmit) by the processor 106 and/or the communication module 112 to an electronic device (e.g., smart phone, handset, wireless voice message system, call light system, etc.) associated with medical personnel (Block 312). For example, the electronic communication may alert medical personnel that the system 100 has determined that the patient is no longer within the bed. In another example, the electronic communication may alert medical personnel that the system 100 has determined that the patient has been positioned on the patient's side for over a defined time period.

Figure 4:
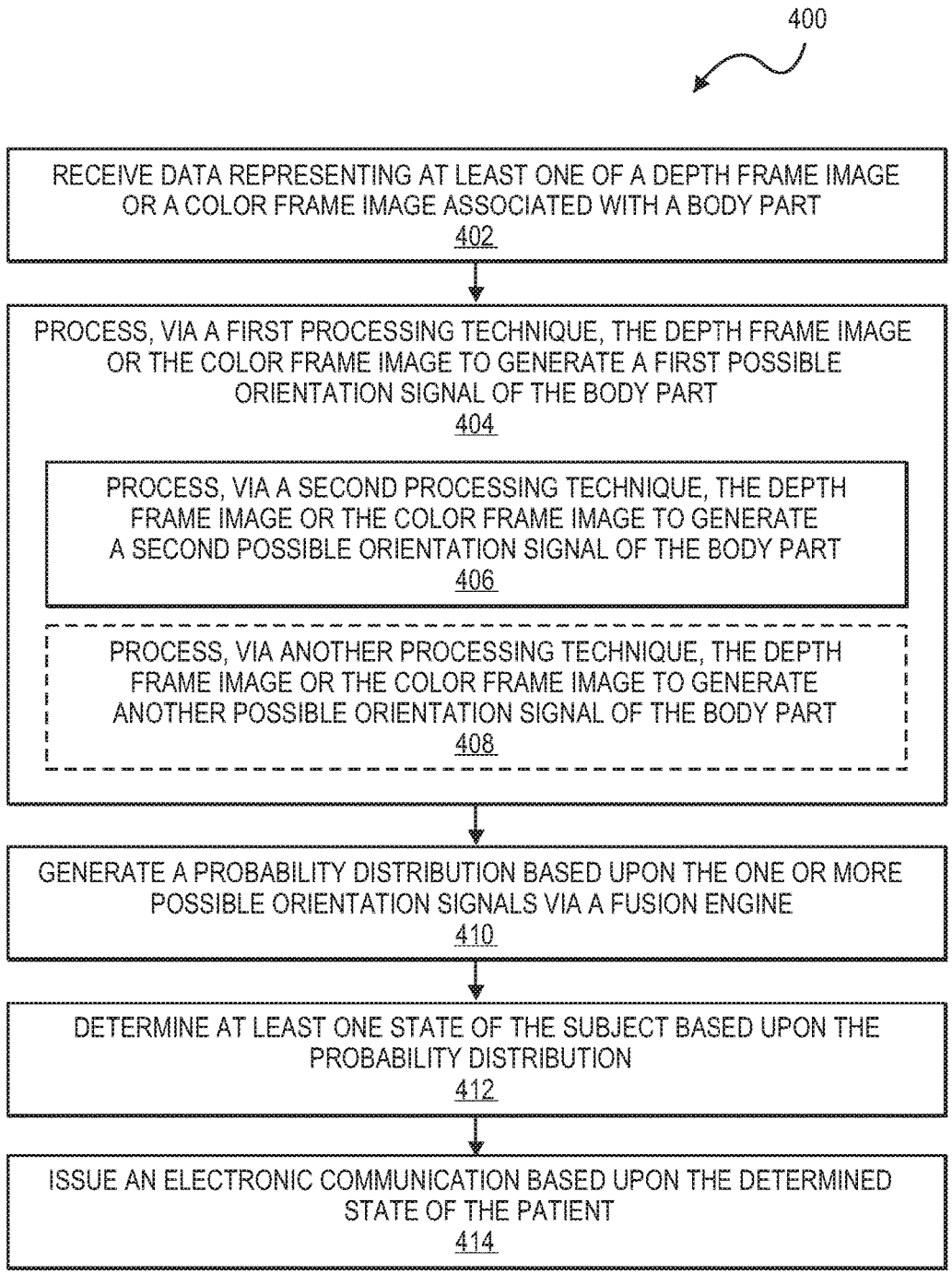
FIG. 4 is a flow diagram illustrating another example method for monitoring a medical environment in accordance with the present disclosure.

FIG. 4 illustrates another example process 400 for determining whether a patient is positioned proximate to a bed utilizing an image capture system, such as the image capture system 100 described above. As shown in FIG. 4, data representing at least one of a depth frame image or a color frame image associated with a body part is received (Block 402). In an implementation, data representing depth frame images and/or color frame images are furnished by an imaging device 102 (e.g., the camera) having an image plane. As shown, the processor processes, via a first processing technique, the depth frame image or the color frame image to generate a first possible orientation signal of the body part with respect to the image plane (Block 404). In an implementation, the processor 106 is configured to process the depth frame image or the color frame image utilizing a first processing technique (e.g., a first processing technique as described above with respect to FIGS. 2J to 2Z) to generate a first possible orientation signal of the body part.

As shown in FIG. 4, the processor processes, via a second processing technique, the depth frame image or the color frame image to generate a second possible orientation signal of the body part with respect to the image plane (Block 406). In an implementation, the processor 106 is configured to process the depth frame image or the color frame image utilizing a second processing technique (e.g., a second processing technique as described above with respect to FIGS. 2J to 2Z) to generate a second possible orientation signal of the body part. In some implementations, the processor processes, via another processing technique (e.g., a third processing technique, a fourth processing technique, a fifth processing technique, etc.), the depth frame image or the color frame image to generate another possible orientation signal of the body part with respect to the image plane (Block 408). The processor generates a probability distribution (e.g., generates a probability distribution) based upon the one or more possible orientation signals via a fusion engine (Block 410). As described above, the processor 106 is configured to generate a probability distribution via the fusion engine 118 based upon at least the first possible orientation signal, the second possible orientation signal, and/or the other possible orientation signals.

The processor determines at least one state of the subject based upon the probability distribution (Block 412). In an implementation, the processor 106 is configured to determine that the subject is in the bed based upon the probability distribution. In another implementation, the processor 106 is configured to determine an orientation of the subject within the bed based upon the probability distribution. In yet another implementation, the processor 106 is configured to determine that the subject is transitioning within the bed or transitioning from/to the bed. As described above, an electronic communication (e.g., e-mail, SMS text, MMS text, HL7 messaging, etc.) is issued (e.g., generate and/or transmit) based upon the determined state of the patient (Block 414).

Figure 5:
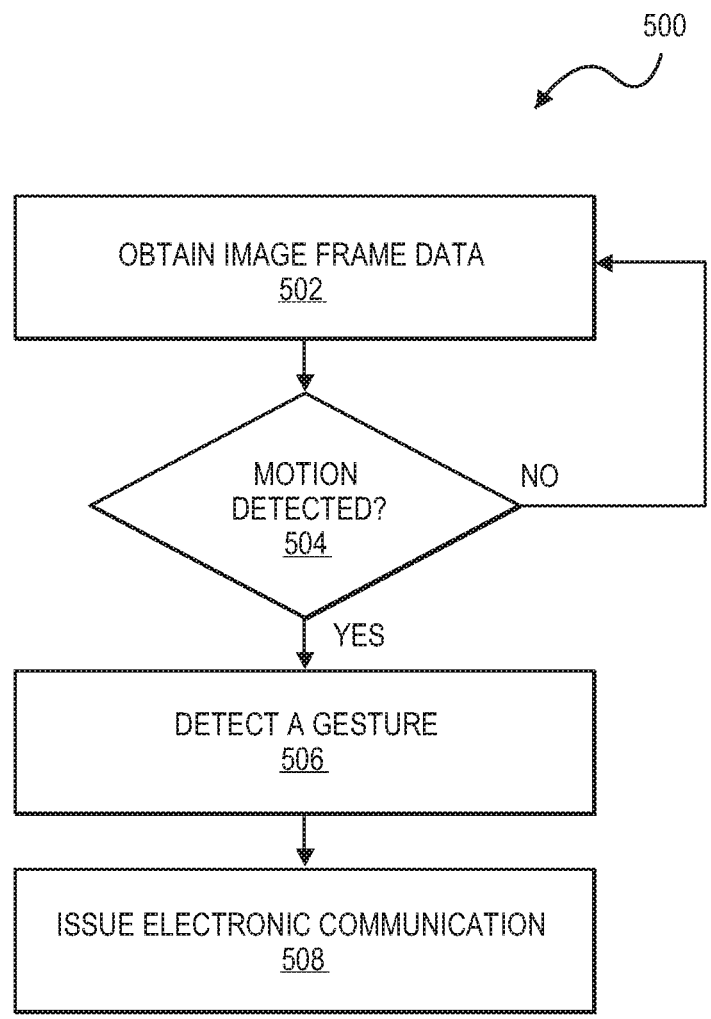
FIG. 5 is a flow diagram illustrating an example method for detecting an action performed by a subject in accordance with the present disclosure.

FIG. 5 illustrates an example process 500 for identifying an action performed by an object, such as a patient. As shown, one or more frame images are obtained from an imaging device (Block 502). A determination is made of whether motion was detected (Decision Block 504). The module 116 is configured to cause the processor 106 to determine whether motion has been detected based upon an identification of pixels representing a specific body part (e.g., an arm) and detecting movement of the pixels representing the specific body part. If no movement is detected (NO from Decision Block 504), the process 500 transitions back to Block 502. If movement is detected (YES from Decision Block 504), a gesture is detected (Block 506). The system 100 is configured to detect the presence or the absence of a gesture. The module 116 causes the processor 106 to track the movement of the identified pixels to determine if the identified pixels correspond to a predetermined movement (e.g., predefined pattern). If the gesture matches a predetermined movement, the processor 106 determines a gesture has been performed (e.g., waving of an arm, movement of a leg, etc.). Once a gesture has been detected, an electronic communication is issued (Block 508). In response to detecting a gesture, the processor 106 provides an indication associated with the presence or the absence of the gesture. For example, the processor 106 issues (e.g., generates and causes transmission) an electronic communication. The electronic communication may be transmitted to medical personnel to indicate that the patient is requesting medical personnel based upon the gesture.

CONCLUSION

Generally, any of the functions described herein can be implemented using hardware (e.g., fixed logic circuitry such as integrated circuits), software, firmware, manual processing, or a combination of these implementations. Thus, the blocks discussed in the above disclosure generally represent hardware (e.g., fixed logic circuitry such as integrated circuits), software, firmware, or a combination thereof. In the instance of a hardware implementation, for instance, the various blocks discussed in the above disclosure may be implemented as integrated circuits along with other functionality. Such integrated circuits may include all of the functions of a given block, system or circuit, or a portion of the functions of the block, system or circuit. Further, elements of the blocks, systems or circuits may be implemented across multiple integrated circuits. Such integrated circuits may comprise various integrated circuits including, but not necessarily limited to: a monolithic integrated circuit, a flip chip integrated circuit, a multichip module integrated circuit, and/or a mixed signal integrated circuit. In the instance of a software implementation, for instance, the various blocks discussed in the above disclosure represent executable instructions (e.g., program code) that perform specified tasks when executed on a processor. These executable instructions can be stored in one or more tangible computer readable media. In some such instances, the entire system, block or circuit may be implemented using its software or firmware equivalent. In other instances, one part of a given system, block or circuit may be implemented in software or firmware, while other parts are implemented in hardware.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A system for monitoring a medical care environment, the system comprising:
   at least one computing device in communication with at least one imaging device, the at least one imaging device having an imaging plane, the at least one imaging device configured to capture a plurality of images comprising a plurality of pixels, the plurality of images representing the medical care environment corresponding to a physical space, the physical space including at least one of a bed or a chair the at least one computing device including:
   a memory configured to store one or more modules;
   a processor coupled to the memory, the processor configured by a fusion engine and the one or more modules to cause the processor to:
   identify one or more first pixels of the plurality of pixels as representing the at least one of the bed or the chair;
   identify one or more second pixels of the plurality of pixels as representing a portion of a body of a subject proximate to the at least one of the bed or the chair;
   process, via a first processing technique, the one or more second pixels to generate a first possible orientation signal of the portion of the body with respect to the imaging plane, the first possible orientation signal representing a position of the portion of the body with respect to the at least one of the bed or the chair;
   process, via a second processing technique via the fusion engine, the one or more second pixels to generate a second possible orientation signal of the portion of the body with respect to the imaging plane, the second possible orientation signal representing the position of the portion of the body with respect to the at least one of the bed or the chair;
   determine a probability distribution based upon the first possible orientation signal and the second possible orientation signal via the fusion engine;
   determine a transitional state of the subject based upon the probability distribution; and
   issue an electronic communication based upon the transitional state of the subject, the electronic communication comprising an alert indicating the transitional state of the subject.

2. The system as recited in claim 1, wherein the processor is further configured to execute the one or more modules to cause the processor to process, via at least one of the first processing technique or the second processing technique, at least one image of the plurality of images to identify a second position corresponding least one of a second subject or an object relative to the subject.

3. The system as recited in claim 1, wherein the processor is further configured to execute the one or more modules to cause the processor to process an image of the plurality of images to detect at least one of a presence or an absence of a gesture; and provide an indication associated with the at least one of the presence or the absence of the gesture.

4. The system as recited in claim 1, wherein the processor is further configured to execute the one or more modules to cause the processor to track the one or more second pixels through the plurality of images; determine an activity parameter of the subject based upon tracking the one or more second pixels; and issue an activity electronic communication indicating the activity parameter when the activity parameter is outside of an activity threshold.

5. The system as recited in claim 1, wherein the plurality of images comprise a plurality of depth frame images.

6. The system as recited in claim 1, wherein the processor is further configured to execute the one or more modules to cause the processor to determine the probability distribution based upon the first possible orientation signal, the second possible orientation signal, and at least one characteristic of the subject via the fusion engine.

7. A method for monitoring a subject within a medical care environment, the method comprising:
   identifying, via a processor configured by a fusion engine, one or more first pixels of a plurality of pixels as representing at least one of a bed or a chair, the plurality of pixels captured by an imaging device, the plurality of pixels representing a physical space;

identifying, via the processor, one or more second pixels of the plurality of pixels as representing a portion of body of the subject proximate to the at least one of the bed or the chair;

processing, via a first processing technique via the processor, the one or more second pixels to generate a first possible orientation signal of the portion of the body with respect to an imaging plane of the imaging device, the first possible orientation signal representing a position of the portion of the body with respect to the at least one of the bed or the chair;

processing, via a second processing technique via the processor, the one or more second pixels to generate a second possible orientation signal of the portion of the body with respect to the imaging plane, the second possible orientation signal representing the position of the portion of the body with respect to the at least one of the bed or the chair;

determining, via the processor, a probability distribution based upon the first possible orientation signal and the second possible orientation signal via the fusion engine;

determining, via the processor, a transitional state of the subject based upon the probability distribution; and issuing, via the processor, an electronic communication based upon the transitional state of the subject, the electronic communication comprising an alert indicating the transitional state of the subject.

8. The method as recited in claim 7, further comprising identifying, via the processor, a presence of a gesture based upon the one or more second pixels; and providing an indication associated with the presence of the gesture.

9. The method as recited in claim 7, further comprising: tracking, via the processor, the one or more second pixels through a plurality of images captured by the imagine device; determining an activity parameter of the subject based upon tracking the one or more second pixels; and issuing an activity electronic communication indicating the activity parameter when the activity parameter is outside of an activity threshold.

10. The method as recited in claim 7, further comprising: processing, via a third processing technique via the processor, the one or more second pixels to generate a third possible orientation signal of the portion of the body, the third possible orientation signal representing the position of the portion of the body with respect to the at least one of the bed or the chair; and determining the probability distribution based upon the first possible orientation signal, the second possible orientation signal, and the third possible orientation signal via the fusion engine.

11. The method as recited in claim 7, wherein determining the probability distribution further comprises determining the probability distribution based upon the first possible orientation signal, the second possible orientation signal, and at least one characteristic of the subject via the fusion engine.

12. The method as recited in claim 11, wherein the at least one characteristic comprises at least one of age, gender, weight, body type, body dimensions, diagnoses, time of day, gait characteristics, mental status, physical restrictions, facial deformities, sleeping abnormalities, angle of bed, dimensions of bed, fall risk score, patient schedule, subject ethnicity, subject skin tone, and bed characteristics.

13. A method for monitoring a medical care environment, the method comprising:

receiving, via a processor configured by a fusion engine, a plurality of images, each image of the plurality of images comprising a plurality of pixels captured by an imaging device having an imaging plane, the plurality of images representing the medical care environment corresponding to a physical space, the physical space including at least one of a bed or a chair;

identifying, via the processor, one or more first pixels of the plurality of pixels as representing the at least one of the bed or the chair;

identifying, via the processor, one or more second pixels of the plurality of pixels as representing a body part of a subject proximate to the at least one of the bed or the chair;

processing, via a first processing technique via the processor, the one or more second pixels to generate a first possible orientation signal of the body part with respect to the imaging plane, the first possible orientation signal representing a position of the body part with respect to the at least one of the bed or the chair;

processing, via a second processing technique via the processor, the one or more second pixels to generate a second possible orientation signal of the body part with respect to the imaging plane, the second possible orientation signal representing the position of the body part with respect to the at least one of the bed or the chair;

determining, via the processor, a probability distribution based upon the first possible orientation signal and the second possible orientation signal via the fusion engine;

determining, via the processor, a transitional state of the subject based upon the probability distribution; and issuing, via the processor, an electronic communication based upon the transitional state of the subject, the electronic communication comprising an alert indicating the transitional state of the subject.

14. The method as recited in claim 13, further comprising:

processing, via a third processing technique via the processor, the one or more second pixels to generate a third possible orientation signal of the body part with respect to the imaging plane, the third possible orientation signal representing the position of the body part with respect to the at least one of the bed or the chair;

processing, via a fourth processing technique via the processor, the one or more second pixels to generate a fourth possible orientation signal of the body part with respect to the imaging plane, the fourth possible orientation signal representing the position of the body part with respect to the at least one of the bed or the chair; and determining, via the processor, the probability distribution based upon the first possible orientation signal, the second possible orientation signal, the third possible orientation signal, and the fourth possible orientation signal via the fusion engine.

15. The method as recited in claim 13, wherein determining the transitional state of the subject based upon the probability distribution comprises determining an activity level associated with the subject.

16. The method as recited in claim 13, wherein determining the transitional state of the subject based upon the probability distribution comprises determining the transitional state of the subject within the bed based upon the probability distribution.

17. The method as recited in claim 13, further comprising identifying, via the processor, one or more third pixels of the plurality of pixels as representing at least one of a second subject or an object relative to the subject.

18. The method as recited in claim 13, further comprising tracking, via the processor, the one or more second pixels through the plurality of images; determining, via the processor, whether the one or more second pixels corresponds to a gesture; and causing issuance of a second electronic communication indicating the gesture has been performed when the one or more second pixels corresponds to the gesture.

\* \* \* \* \*